(12) United States Patent
Pudil et al.

(10) Patent No.: US 9,827,361 B2
(45) Date of Patent: Nov. 28, 2017

(54) PH BUFFER MEASUREMENT SYSTEM FOR HEMODIALYSIS SYSTEMS

(71) Applicant: MEDTRONIC, INC., Minneapolis, MN (US)

(72) Inventors: Bryant J. Pudil, Plymouth, MN (US); Thomas E. Meyer, Stillwater, MN (US); David B. Lura, Maple Grove, MN (US); Martin T. Gerber, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 451 days.

(21) Appl. No.: 13/837,287

(22) Filed: Mar. 15, 2013

(65) Prior Publication Data

US 2014/0220699 A1 Aug. 7, 2014

Related U.S. Application Data

(60) Provisional application No. 61/760,078, filed on Feb. 2, 2013.

(51) Int. Cl.
*A61M 1/16* (2006.01)
*A61M 1/28* (2006.01)
*G01N 33/84* (2006.01)

(52) U.S. Cl.
CPC ........ *A61M 1/1656* (2013.01); *A61M 1/1605* (2014.02); *A61M 1/1658* (2013.01);
(Continued)

(58) Field of Classification Search
CPC .............. A61M 1/1656; A61M 1/1658; A61M 1/1696; A61M 1/287; A61M 1/16;
(Continued)

(56) References Cited

U.S. PATENT DOCUMENTS 3,608,729 A 9/1971 Haselden
3,669,878 A 6/1972 Marantz
(Continued)

FOREIGN PATENT DOCUMENTS

DE 3215003 4/1985
EP 266795 A2 11/1987
(Continued)

OTHER PUBLICATIONS

Understanding Dialysate Bicarbonate—A simple approach to undersating a complex equation by Fresenius Medical Care, 2011.*
(Continued)

*Primary Examiner* — Robert Clemente
*Assistant Examiner* — Akash Varma

(57) ABSTRACT

A pH-buffer measurement system that has at least one source for modifying the pH of a fluid entering the system, the source selected from an acid source and a base source. The acid source adds an acid equivalent to provide an acid reacted fluid and the base source adds a base equivalent to provide a base reacted fluid. The source is in fluid communication with a flow path and a component for determining a fluid characteristic of the acid reacted fluid or the base reacted fluid. The fluid characteristic that is measured is any one of a gas phase pressure, an electrical conductivity, or thermal conductivity.

46 Claims, 9 Drawing Sheets

(52) U.S. Cl.
CPC .......... *A61M 1/1696* (2013.01); *A61M 1/287*
(2013.01); *G01N 33/84* (2013.01); *A61M*
*2205/3317* (2013.01); *A61M 2205/7518*
(2013.01)

(58) Field of Classification Search
CPC .......... A61M 1/28; G01N 33/84; G01N 7/00;
G01N 27/02; G01N 25/18
USPC ....... 210/96.2, 647, 743; 422/68.1; 436/163;
604/29
See application file for complete search history.

(56) References Cited

U.S. PATENT DOCUMENTS

| | | |
|---|---|---|
| 3,669,880 A | 6/1972 | Marantz |
| 3,692,648 A | 9/1972 | Matloff |
| 3,776,819 A | 12/1973 | Williams |
| 3,850,835 A | 11/1974 | Marantz |
| 3,884,808 A | 5/1975 | Scott |
| 3,902,490 A | 9/1975 | Jacobsen et al. |
| 3,939,069 A | 2/1976 | Granger |
| 3,989,622 A | 11/1976 | Marantz |
| 4,060,485 A | 11/1977 | Eaton |
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,750,494 A | 6/1988 | King |
| 4,816,162 A | 3/1989 | Rosskopf et al. |
| 4,826,663 A | 5/1989 | Alberti |
| 4,828,693 A | 5/1989 | Lindsay |
| 4,900,308 A | 2/1990 | Verkaart |
| 4,977,888 A | 12/1990 | Rietter |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,230,702 A | 7/1993 | Lindsay et al. |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,419,347 A | 5/1995 | Carruth |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,835 A | 11/1997 | Brugger |
| 5,702,536 A | 12/1997 | Carruth |
| 5,744,031 A | 4/1998 | Bene |
| 5,762,782 A | 6/1998 | Kenley |
| 5,849,179 A | 12/1998 | Emerson et al. |
| 5,858,186 A | 1/1999 | Glass |
| 5,944,684 A | 8/1999 | Roberts |
| 5,948,251 A | 9/1999 | Brugger |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau et al. |
| 6,230,059 B1 | 5/2001 | Duffin |
| 6,248,093 B1 | 6/2001 | Moberg |
| 6,254,567 B1 | 7/2001 | Treu |
| 6,264,680 B1 | 7/2001 | Ash |
| 6,321,101 B1 | 11/2001 | Holmstrom |
| 6,362,591 B1 | 3/2002 | Moberg |
| 6,363,279 B1 | 3/2002 | Ben-Haim |
| 6,521,184 B1 | 2/2003 | Edgson et al. |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,711,439 B1 | 3/2004 | Bradley |
| 6,719,745 B1 | 4/2004 | Taylor |
| 6,726,647 B1 | 4/2004 | Sternby |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,861,266 B1 | 3/2005 | Sternby |
| 6,878,283 B2 | 4/2005 | Thompson |
| 6,960,179 B2 | 11/2005 | Gura |
| 7,033,498 B2 | 4/2006 | Wong |
| 7,074,332 B2 | 7/2006 | Summerton |
| 7,077,819 B1 | 7/2006 | Goldau |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,326,576 B2 | 2/2008 | Womble et al. |
| 7,435,342 B2 | 10/2008 | Tsukamoto |
| 7,488,447 B2 | 2/2009 | Sternby |
| 7,500,958 B2 | 3/2009 | Asbrink |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum |
| 7,785,463 B2 | 8/2010 | Bissler |
| 7,790,103 B2 | 9/2010 | Shah |
| 7,794,141 B2 | 9/2010 | Perry |
| 7,794,419 B2 | 9/2010 | Paolini et al. |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,290 B2 | 6/2011 | Karoor et al. |
| 7,955,291 B2 | 6/2011 | Sternby |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,029,454 B2 | 10/2011 | Kelly et al. |
| 8,034,161 B2 | 10/2011 | Gura |
| 8,066,658 B2 | 11/2011 | Karoor et al. |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |

(56) References Cited

U.S. PATENT DOCUMENTS

| | | |
|---|---|---|
| 8,303,532 B2 | 11/2012 | Hamada et al. |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding et al. |
| 8,409,441 B2 | 4/2013 | Wilt |
| 8,409,444 B2 | 4/2013 | Wong |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann et al. |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 * | 12/2014 | Crnkovich .......... A61M 1/1656 210/100 |
| 9,144,640 B2 | 9/2015 | Pudil |
| 2002/0042561 A1 | 4/2002 | Schulman |
| 2002/0112609 A1 | 8/2002 | Wong |
| 2003/0010717 A1 | 1/2003 | Brugger |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers |
| 2004/0068219 A1 | 4/2004 | Summerton |
| 2004/0099593 A1 | 5/2004 | DePaolis |
| 2004/0102732 A1 | 5/2004 | Naghavi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 6/2005 | Childers |
| 2005/0131331 A1 | 6/2005 | Kelly |
| 2005/0131332 A1 | 6/2005 | Kelly |
| 2005/0150832 A1 | 7/2005 | Tsukamoto |
| 2005/0234381 A1 | 10/2005 | Niemetz |
| 2005/0236330 A1 | 10/2005 | Nier |
| 2005/0274658 A1 | 12/2005 | Rosenbaum |
| 2006/0025661 A1 | 2/2006 | Sweeney |
| 2006/0195064 A1 | 8/2006 | Plahey |
| 2006/0217771 A1 | 9/2006 | Soykan |
| 2006/0226079 A1 | 10/2006 | Mori |
| 2006/0241709 A1 | 10/2006 | Soykan et al. |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1 | 9/2007 | Curtin |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0101577 A1 | 4/2009 | Fulkerson |
| 2009/0105629 A1 | 4/2009 | Grant |
| 2009/0124963 A1 | 5/2009 | Hogard |
| 2009/0127193 A1 | 5/2009 | Updyke |
| 2009/0157877 A1 | 6/2009 | Baek |
| 2009/0171261 A1 | 7/2009 | Sternby |
| 2009/0182263 A1 | 7/2009 | Burbank |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |
| 2010/0030151 A1 | 2/2010 | Kirsch |
| 2010/0042035 A1 | 2/2010 | Moissl |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0102190 A1 | 4/2010 | Zhu et al. |
| 2010/0114012 A1 | 5/2010 | Sandford |
| 2010/0130906 A1 | 5/2010 | Balschat |
| 2010/0137693 A1 | 6/2010 | Porras |
| 2010/0137782 A1 | 6/2010 | Jansson |
| 2010/0168546 A1 | 7/2010 | Kamath |
| 2010/0192686 A1 | 8/2010 | Kamen |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0274171 A1 | 10/2010 | Caleffi |
| 2010/0312174 A1 | 12/2010 | Hoffman |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann et al. |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120930 A1 | 5/2011 | Mishkin |
| 2011/0120946 A1 | 5/2011 | Levin |
| 2011/0130666 A1 | 6/2011 | Dong |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0184340 A1 | 7/2011 | Tan |
| 2011/0220562 A1 | 9/2011 | Beiriger |
| 2011/0272337 A1 | 11/2011 | Palmer |
| 2011/0297593 A1 | 12/2011 | Kelly |
| 2011/0315611 A1 | 12/2011 | Fulkerson |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0115248 A1 * | 5/2012 | Ansyln et al. ................ 436/501 |
| 2012/0220528 A1 | 8/2012 | VanAntwerp |
| 2012/0248017 A1 | 10/2012 | Beiriger |

(56) References Cited

U.S. PATENT DOCUMENTS

| | | |
|---|---|---|
| 2012/0258545 A1 | 10/2012 | Ash |
| 2012/0258546 A1* | 10/2012 | Marran et al. .............. 436/163 |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan et al. |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0018301 A1 | 1/2013 | Weaver |
| 2013/0019994 A1 | 1/2013 | Schaer |
| 2013/0037465 A1 | 2/2013 | Heyes |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228517 A1 | 9/2013 | Roger |
| 2013/0231607 A1 | 9/2013 | Roger |
| 2013/0248426 A1 | 9/2013 | Pouchoulin |
| 2013/0274642 A1 | 10/2013 | Soykan |
| 2013/0304020 A1 | 11/2013 | Wilt |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur et al. |
| 2014/0065950 A1 | 3/2014 | Mendelsohn |
| 2014/0088442 A1 | 3/2014 | Soykan et al. |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0251908 A1 | 9/2014 | Ding |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |

FOREIGN PATENT DOCUMENTS

| | | |
|---|---|---|
| EP | 0743071 | 11/1996 |
| EP | 1124599 | 5/2000 |
| EP | 1175238 | 11/2000 |
| EP | 711182 B1 | 6/2003 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2388030 | 11/2011 |
| EP | 2576453 A2 | 12/2011 |
| EP | 2701580 | 11/2012 |
| EP | 2701595 | 11/2012 |
| EP | 1545652 B1 | 1/2013 |
| EP | 1345856 B1 | 3/2013 |
| EP | 2344220 B1 | 4/2013 |
| EP | 1351756 | 7/2013 |
| EP | 2190498 | 7/2013 |
| EP | 1414543 | 9/2013 |
| EP | 2701596 | 3/2014 |
| EP | 1787666 | 11/2015 |
| JP | 5099464 | 10/2012 |
| WO | 9532010 A1 | 11/1995 |
| WO | 9937342 | 7/1999 |
| WO | 0057935 | 10/2000 |
| WO | 0066197 | 11/2000 |
| WO | 0066197 A1 | 11/2000 |
| WO | 0170307 A1 | 9/2001 |
| WO | 0185295 A2 | 9/2001 |
| WO | 0185295 A2 | 11/2001 |
| WO | 03043677 A2 | 5/2003 |
| WO | 2003043680 | 5/2003 |
| WO | 03051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | 2004105589 A2 | 12/2004 |
| WO | 2005061026 | 7/2005 |
| WO | 2005123230 A2 | 12/2005 |
| WO | 2006124431 A2 | 11/2006 |
| WO | 2007010164 A2 | 1/2007 |
| WO | 2007089855 A2 | 8/2007 |
| WO | 2007146162 A2 | 12/2007 |
| WO | 2007146162 A3 | 12/2007 |
| WO | 2008037410 | 4/2008 |
| WO | 2009024566 | 2/2009 |
| WO | 2009026603 | 3/2009 |
| WO | 2009026603 A1 | 3/2009 |
| WO | 2009061608 | 5/2009 |
| WO | 2009064984 | 5/2009 |
| WO | 2009067071 A1 | 5/2009 |
| WO | 2009071103 | 6/2009 |
| WO | 2009094184 | 7/2009 |
| WO | 2009132839 A1 | 11/2009 |
| WO | 2009157877 | 12/2009 |
| WO | 2009157878 | 12/2009 |
| WO | 2010028860 A1 | 3/2010 |
| WO | 2010042666 A2 | 4/2010 |
| WO | 2010096659 | 10/2010 |
| WO | 2010121820 | 10/2010 |
| WO | 2010102190 A4 | 11/2010 |
| WO | 2011025705 A1 | 3/2011 |
| WO | 2012042323 | 4/2012 |
| WO | 2012050781 | 4/2012 |
| WO | 2012051996 | 4/2012 |
| WO | 2012067585 | 5/2012 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013027214 | 2/2013 |
| WO | 2013028809 A3 | 2/2013 |
| WO | 2013019994 A3 | 4/2013 |
| WO | 2013025844 A3 | 5/2013 |
| WO | 2013103607 A1 | 7/2013 |
| WO | 2013103906 | 7/2013 |

(56) References Cited

FOREIGN PATENT DOCUMENTS

| WO | 2013110906 | | 8/2013 |
|---|---|---|---|
| WO | 2013110919 | | 8/2013 |
| WO | 2013114063 | A | 8/2013 |
| WO | 2013121162 | A1 | 8/2013 |
| WO | 2013140346 | | 9/2013 |
| WO | 2013141896 | | 9/2013 |
| WO | 2013188861 | A1 | 12/2013 |
| WO | 2014066254 | | 5/2014 |
| WO | 2014066255 | | 5/2014 |
| WO | 2014077082 | | 5/2014 |
| WO | 2014117000 | | 7/2014 |
| WO | 2014121162 | | 8/2014 |
| WO | 2014121163 | | 8/2014 |
| WO | 2014121167 | | 8/2014 |
| WO | 2014121169 | | 8/2014 |

OTHER PUBLICATIONS

PCT/US2014/014357 International Search Report and Written Opinion.
U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/757,792, filed Feb. 2, 2013.
U.S. Appl. No. 13,837,287, filed Mar. 15, 2013.
Bleyer, et. al., Sudden and cardiac death rates in hemodialysis patients, Kidney International, 1999, 1553-1559 : 55.
Maclean, et, al., Effects of hindlimb contraction on pressor and muscle interstitial metabolite responses in the cat, J. App. Physiol., 1998, 1583-1592, 85 (4).
Overgaard, et. al., Activity-induced recovery of excitability in K+-depressed rat soieus muscle, Am. J. Physiol. Regulatory integrative Comp. Physiol., 2001, R48-R55, vol. 280.
Overgaard. et. al., Relations between excitability and contractility in rate soleus'muscle: role of the Na+-K+ pump and Na+-K-S gradients. Journal of Physiology, 1999, 215-225, 518(1).
PCT/US2012/034330, International Search Report, dated Aug. 28, 2012.
PCT/US2012/034332, International Search Report, dated Jul. 5, 2012.
Roberts M, The regenerative dialysis (REDY) sorbent system. Nephrology, 1998, 275-278:4.
Ronco, et. al., "Cardiorenal Syndrome", J. Am. Coll. Cardiol., 2008, 1527-1539 : 52.
Siegenthalar, et. al., Pulmonary fluid status monitoring with intrathoracic impedance, Journal of Clinical Monitoring and Computing, 2010, 449-451 : 24.
U.S. Appl. No. 60/650,497.
U.S. Appl. No. 61/480,535.
U.S. Appl. No. 61/480,539.
U.S. Appl. No. 61/480,541.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Wang, Fundamentals of intrathoracic impedance monitoring in heart failure, Am. J. Cardiology, 2007, 3G-310: Suppl.
Brynda, et. al., The detection of toman 2-microglcbuiin by grating coupler immunosensor with three dimensional antibody networks. Biosensors & Bioelectronics, 1999, 363-368, 14(4).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, dated Aug. 13, 2013.
PCT/US/2012/034329, International Search Report, dated Dec. 3, 2012.
PCT/US2012/034331, International Search Report, dated Jul. 9, 2012.
PCT/US2012/034334, International Search Report, dated Jul. 6, 2012.
Redfield, et. al, "Restoration of renal response to atria! natriuretic factor in experimental low-output heat failure", Am. J. Physiol., 1989, R917-923 : 257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Leifer, I., et al., A Study on the Temperature Variation of Rise Velocity for Large Clean Bubbles, J. Atmospheric & Oceanic Tech., vol. 17, pp. 1392-1402.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Talaia, MAR, Terminal Velocity of a Bubble Rise in a Liquid Column, Talaia, World Acad. of Sci., Engineering & Tech., vol. 28, pp. 264-68.
The FHN Trial Group. In-Center. Hemodialysis Six Times per Week versus Three Times per Week, New England Journal of Medicine, 2010.
U.S. Appl. No. 13/757,693, filed Feb. 1, 2013.
Coast, et al. 1990, An approach to Cardiac Arrhythmia analysis Using Hidden Markov Models, IEEE Transactions on Biomedical Engineering. 1990, 37 (9):826-835.
PCT/US2012/034330, International Preliminary Report on Patentability, Oct. 29, 2013.
PCT Application, PCT/US20013/020404, filed Jan. 4, 2013.
U.S. Appl. No. 14/261,651, filed Apr. 25, 2014.
U.S. Appl. No. 14/259,655, filed Apr. 23, 2014.
PCT/US2012/034333, International Preliminary Report on Patentability, Oct. 29, 2013.
PCT/US2012/034333, International Search Report, Aug. 29, 2013.
U.S. Appl. No. 13/424,429.
U.S. Appl. No. 13/424,479.
U.S. Appl. No. 61/480,528.
U.S. Appl. No. 61/480,530.
U.S. Appl. No. 61/480,532.
Wang, Fundamentals of intrathoracic impedance monitoring in heart failure, Am. J. Cardiology, 2007, 3G-10G : Suppl.
U.S. Appl. No. 13/368,225.
U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
ISA Invitation to Pay Additional Fees, PCT/US2012/034323 dated Aug. 2, 2012.
Weissman, S., et al., "Hydroxyurea-induced hepatitis in human immunodeficiency virus-positive patients." Clin. Infec. Dis, (Jul. 29, 1999): 223-224.
Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
PCT/US2014/067650 International Search Report Written Opinion dated Mar. 9, 2015.
PCT/US2012/034335, International Search Report, dated Sep. 5, 2012.
U.S. Appl. No. 61/480,544.
U.S. Appl. No. 13/424,525.
U.S. Appl. No. 13/836,973, filed Mar. 15, 2013.

(56) References Cited

OTHER PUBLICATIONS

U.S. Appl. No. 14/259,589, filed Apr. 23, 2014.
Gambro AK 96 Dialysis Machine Operator's Manual, Dec. 2012.
EP13182115.9-1651 European Search Report, dated Feb. 3, 2014.
Written Opinion of the International Searching Authority for PCT/US2012/049398 dated Feb. 25, 2013.
European Search Report 12819714.2-1651/2739325 PCT/US2012049398, dated Jun. 12, 2015.
PCT/US2014/14343 Int'l Search Report & Written Opinion, dated Sep. 2006.
EP 14746791 Supplementary European Search Report dated Aug. 19, 2016.
PCT/US2014/014350 International Search Report and Written Opinion dated May 2014.
EP 14746793 Supplementary European Search Report dated Aug. 18, 2016.
U.S. Appl. No. 29/446,285, filed Feb. 1, 2013.
International Search Report from PCT/US2012/051946.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2014/014345 International Search Report and Written Opinion, dated May 2014.
EP 14746799 Supplementary European Seach Report dated Aug. 18, 2016.
PCT/US2013/020404, International Search Report, dated Jan. 4, 2013.
Welgemoed, T.J., "Capacitive Deionization Technology: An Alternative to desalination Solution," Desalination 183 (2005) 327-340.
Office Action in Chinese Application 201480007139.2 dated May 31, 2017.
Office Action in Chinese Application 201480007136.3 dated Jun. 15, 2017.
Office Action in Chinese Application 201480007132.5 dated Jul. 19, 2017.
Examination Report in Australian Application 2014212141 dated May 26, 2017.

* cited by examiner

PH BUFFER MEASUREMENT SYSTEM FOR HEMODIALYSIS SYSTEMS

CROSS-REFERENCE

This application claims the priority of U.S. Provisional Application No. 61/760,078 filed on Feb. 2, 2013, the entire content thereof is incorporated herein by reference.

FIELD OF THE INVENTION

The invention relates to systems and methods for measuring the pH and buffer concentration of a dialysate fluid during any one hemodialysis, hemofiltration, hemodiafiltration and peritoneal dialysis by determining a fluid characteristic of an acid reacted fluid or a base reacted fluid.

BACKGROUND

During fluid therapies such as hemodialysis, hemofiltration, hemodiafiltration and peritoneal dialysis, the dialysate pH and buffer concentration can play a critical role in patient outcomes. The dialysate pH and buffer concentration are prescribed for a patient based on the acid-base status of the patient. Acidotic patients can be treated by increasing their bicarbonate buffer levels in the dialysate and patients with alkalosis can be treated by decreasing their bicarbonate levels in the dialysate. A method to measure pH and buffer dialysate concentration is especially important with systems that contain a component that may change the pH level and bicarbonate concentration to unknown values. For example, regenerative hemodialysis systems, such as the Recirculating Dialysate System ("REDY" System), contain sorbent materials that release and/or remove hydrogen ions and bicarbonate from the dialysate fluid. The removal and/or addition of hydrogen ions and bicarbonate to the dialysate fluid depend on several factors including: patient blood urea level, patient weight, dialysate composition, sorbent properties, etc. Because of this, it becomes difficult to predict the changes in dialysate pH and bicarbonate concentration that will occur during a hemodialysis session. Therefore, there is a need for systems and methods that can measure the pH and bicarbonate concentration of the dialysate.

SUMMARY OF THE INVENTION

The invention is directed towards a pH-buffer measurement system that can have at least one source for modifying the pH of a fluid entering the system, the source selected from an acid source and a base source wherein the acid source adds an acid equivalent to provide an acid reacted fluid and the base source adds a base equivalent to provide a base reacted fluid wherein the source is in fluid communication with a flow path; and a component for determining a fluid characteristic of the acid reacted fluid or the base reacted fluid; wherein the fluid characteristic that can be measured is any one of a gas phase pressure, an electrical conductivity, or thermal conductivity.

In any embodiment, the component can determine a fluid characteristic of an unreacted fluid. In any embodiment, a static mixer can be provided downstream from the at least one source for modifying the pH of the fluid entering the system.

In any embodiment, the system can have one or more pumps for pumping fluid into and out of the system.

In any embodiment, the system can determine a pH, buffer content or both of the fluid by taking a difference in a first value of the fluid characteristic of the fluid entering the system and a second value of the fluid characteristic of the acid reacted fluid or the base reacted fluid.

In any embodiment, the system can determine a pH, buffer content or both of the fluid by taking a difference in a first value of the fluid characteristic of the fluid entering the system and a second value of the fluid characteristic of an unreacted fluid.

In any embodiment, the component can measure a gas phase pressure above the fluid entering the system.

In any embodiment, a component of the system can measure a gas phase pressure above the acid reacted fluid or the base reacted fluid. In any embodiment, the component can measure a thermal conductivity of the fluid entering the system.

In any embodiment, the component can measure a thermal conductivity of the acid reacted fluid or the base reacted fluid. In any embodiment, the component can measure the thermal conductivity when it is flushed with a purge gas wherein the gas to be measured diffuses from the fluid entering the system, the acid reacted fluid or the base reacted fluid through a membrane that can change the thermal conductivity of a gas surrounding the electrode.

In any embodiment, the rate of change of the thermal conductivity can be used to calculate the concentration of a gas.

In any embodiment, the component can measure an electrical conductivity of the acid reacted fluid or the base reacted fluid. In any embodiment, the component can measure an electrical conductivity of the fluid entering the system.

In any embodiment, the fluid entering the system can be dialysate or an ultrafiltrate or fluid used in peritoneal dialysis.

In any embodiment, the buffer content to be measured can be bicarbonate. In any embodiment, the acid source can be added in a predetermined amount to ensure complete conversion of bicarbonate in the fluid entering the system.

In any embodiment, the acid source can add any one of acetic acid, citric acid, hydrochloric acid, or phosphoric acid.

In any embodiment, the component can have a first measurement chamber to measure a gas phase pressure of the acid reacted fluid or the base reacted fluid, and a second measurement chamber to measure the gas phase pressure of the fluid entering the system.

In any embodiment, the system can have a differential pressure sensor in fluid communication with the first and second measurement chamber.

In any embodiment, the system can have a first or second measurement chamber that has an air-gap above a gas permeable membrane in fluid communication with a pressure transducer and a vent valve to allow gas to escape from the first or second measurement chamber wherein the pressure transducer can measure a pressure of the gas phase above any one of the acid reacted fluid, the base reacted fluid, or the fluid entering the system.

In any embodiment, a control system can be provided to perform calculations necessary for determining a fluid characteristic based on any one of the acid reacted fluid, the base reacted fluid, or the fluid entering the system.

In any embodiment, a fluid therapy system is described that can have a dialyzer and a sorbent system in fluid communication with any of the pH-buffer measurement system described herein to form a dialysate flow path wherein the pH-buffer measurement system can determine the pH, buffer concentration or both of any one of the acid reacted fluid, the base reacted fluid, or the fluid entering the pH-buffer measurement system.

In any embodiment, a reconstitution system can be provided for a controlled amount of buffer to be added to a dialysate to form a dialysate with a predetermined concentration of a buffer prior to use in the dialyzer.

In any embodiment, the buffer can be bicarbonate. In any embodiment, the system can have a pH-buffer measurement system that can be positioned downstream from the sorbent system and a degasser.

In any embodiment the reconstitution system can adjust the pH and bicarbonate concentration to desired levels.

In any embodiment, a conductivity sensor can be connected anywhere along the dialysate flow path.

In any embodiment, fluid in the dialysate flow path can be selectively metered into and out of the dialysate flow path. In any embodiment, the system can be a controlled compliant system. In any embodiment, fluid in the dialysate flow path can be selectively metered into and out of the dialysate flow path.

In any embodiment, any of the systems described herein can be used for any one of hemodialysis, hemofiltration, hemodiafiltration and peritoneal dialysis.

The present invention in one or more embodiments also relates to a fluid therapy system comprising a fluid flow path in fluid communication with a dialyzer, a sorbent regeneration unit, and a fluid characteristic management unit, the fluid characteristic management unit being positioned between the sorbent regeneration unit and the dialyzer along a fluid flow.

In any embodiment, the fluid characteristic management unit of the fluid therapy system is a pH-buffer management unit.

In any embodiment, the fluid characteristic management unit of the fluid therapy system is a potassium management unit.

In any embodiment, the fluid therapy system can further include a degasser in fluid communication with the fluid flow loop and being positioned downstream of the sorbent regeneration unit along the fluid flow.

In any embodiment, the fluid therapy system can further include a bypass flow path diverting a portion of the fluid flow from the fluid characteristic management unit.

In any embodiment, the fluid therapy system can further include a conductivity sensor in fluid communication with the fluid flow path and being positioned downstream of the fluid characteristic management unit along the fluid flow.

In any embodiment, the fluid characteristic management unit of the fluid therapy system can include at least one of an inlet for an acid feed and an inlet for a base feed.

In any embodiment, the fluid characteristic management unit of the fluid therapy system can include at least one of a thermal conductivity sensor and an electrical conductivity sensor.

In any embodiment, the fluid therapy system can further include a replacement flow loop in fluid communicating with the fluid flow path and positioned downstream of the fluid characteristic management unit, the replacement flow loop transporting a portion of a regenerated fluid out of the sorbent regeneration unit directly back into the blood of a subject and bypassing the dialyzer.

In any embodiment, the fluid therapy system can further include an open dialysate reservoir in fluid communication with the fluid flow path and being positioned upstream of the sorbent regeneration unit along the fluid flow.

In any embodiment, a method for determining a pH or buffer content of a fluid is described that can have the step of modifying the pH of a fluid by adding an acid equivalent to provide an acid reacted fluid or adding a base equivalent to provide a base reacted fluid; and determining at least one fluid characteristic of the acid reacted fluid or the base reacted fluid by taking a difference in a first value of the fluid characteristic and a second value of the fluid characteristic of the acid reacted fluid or the base reacted fluid In any embodiment, the step is described for recirculating the acid reacted fluid or the base reacted fluid to allow complete reaction between the bicarbonate and an acid to form carbon dioxide to form a recirculated fluid; measuring the pressure of the recirculated fluid reading to determine an amount of carbon dioxide contained in the recirculated fluid.

In any embodiment, the step is described for recirculating the dialysate to determine total pressure of gases in equilibrium with the dialysate; acidifying the dialysate to convert all of the bicarbonate to carbon dioxide; and measuring a total pressure of gases in equilibrium with the dialysate with a pressure sensor; and determining the partial pressure of carbon dioxide in the dialysate.

In any embodiment, the step is described for flowing the fluid through a static mixer to enhance the mixing between an acid solution and the dialysate.

In any embodiment, the step is described for flowing the fluid through any one of a fluid path for hemodialysis, hemofiltration, hemodiafiltration and peritoneal dialysis.

BRIEF DESCRIPTION OF THE DRAWINGS

Throughout the figures and the specification, components with the same numbers in the FIG.'s refer to the same components.

DETAILED DESCRIPTION

Definitions

Figure 1:
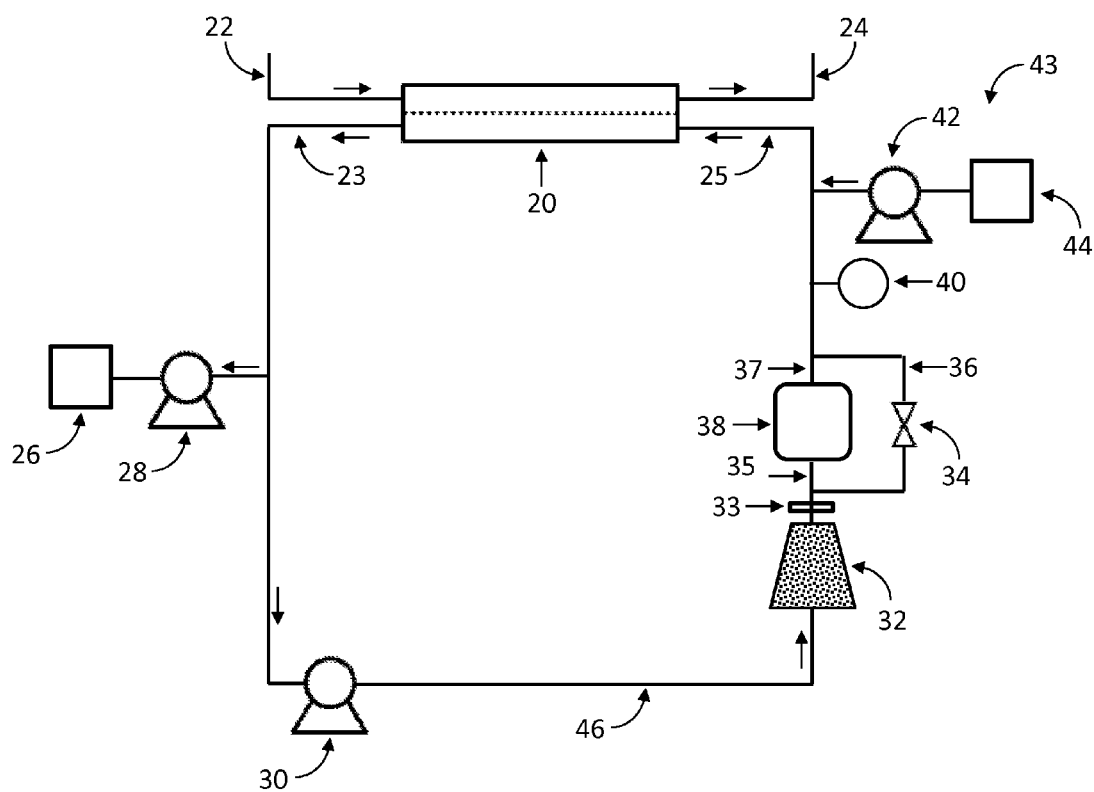
FIG. 1 is a flow diagram of a dialysate regeneration system with a controlled compliant dialysate flow path and a pH-buffer measurement system.

Unless defined otherwise, all technical and scientific terms used herein generally have the same meaning as commonly understood by one of ordinary skill in the relevant art. The definitions provided herein should not be rigidly construed without taking into account the context and other ascribed meanings provided, or by their use, in other parts of the specification, claims, and drawings.

The articles "a" and "an" are used herein to refer to one or to more than one (i.e., to at least one) of the grammatical object of the article. By way of example, "an element" means one element or more than one element.

The term "acid or base equivalents" refers to an equivalent acid or base donating or accepting an equal number of moles of hydrogen or hydronium ions per mole of the acid to which the equivalent acid is being equated, or mole of hydroxide ions to which the equivalent base is being equated.

The term "acid feed" refers a state of fluid communication that enables an acid solution to be obtained from an acid source and connected or fed into a receiving source or flow path.

An "acid" can be either an Arrhenius acid, a Brzønsted-Lowry acid, or a Lewis acid. The Arrhenius acids are substances or fluids which increase the concentration of hydronium ions ($H_3O^+$) in solution. The Brønsted-Lowry acid is a substance which can act as a proton donor. Lewis acids are electron-pair acceptors.

The term "activated carbon" may refer to a porous carbon material having a surface area greater than 500 $m^2$ per gram. Activated carbon can be capable of absorbing several species including heavy metals such as lead, mercury, arsenic, cadmium, chromium and thallium among others, oxidants such as chlorine and chloramines, fluoride ions, and waste species such as phosphate and certain nitrogen-containing waste species such as creatinine and uric acid.

The terms "administering," "administer," "delivering," "deliver," "introducing," and "introduce" can be used, in context, interchangeably to indicate the introduction of water or a dialysate having an altered concentration of at least one component, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a diffusion membrane or other means.

An "acid source" can be either source of an Arrhenius acid, a Brønsted-Lowry acid, or a Lewis acid. The Arrhenius acids are substances or fluids which increase the concentration of hydronium ions ($H_3O^+$) in solution. The Brønsted-Lowry acid is a substance which can act as a proton donor. Lewis acids are electron-pair acceptors.

A "base source" can be either source of a substance that can accept hydrogen cations (protons) or more generally, donate a pair of valence electrons. A soluble base is referred to as an alkali if it contains and releases hydroxide ions ($OH^-$) quantitatively. The Brønsted-Lowry theory defines bases as proton (hydrogen ion) acceptors, while the more general Lewis theory defines bases as electron pair donors, allowing other Lewis acids than protons to be included. The Arrhenius bases act as hydroxide anions, which is strictly applicable only to alkali.

The term "base feed" refers a state of fluid communication that enables a base solution to be obtained from a base source and connected or fed into a receiving source or flow path.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "controller," "control unit," "processor," or "microprocessor" is a device which monitors and affects the operational conditions of a given system. The operational conditions are typically referred to as output variables of the system wherein the output variables can be affected by adjusting certain input variables.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if the patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, and as discussed herein and shown in the drawings is that the controlled compliant system can move fluids bi-directionally. In certain cases, the bi-directional fluid movement is across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

A "gas permeable membrane" is a membrane that selectively allows gases to pass through the membrane while providing a barrier to fluids.

"Gas phase pressure" also known as "vapor" is the equilibrium pressure from a liquid or a solid at a specific temperature. If the vapor is in contact with a liquid or solid phase, the two phases will be in a state of equilibrium.

The term "fluid characteristic" refers to any chemical or biological components that make up or can be found dissolved or suspended in the fluid or gas properties associated with the fluid; or to any physical property of the fluid including, but not limited to temperature, pressure, general or specific conductivities associated with the fluid or related gases.

The terms "pH-buffer measurement system" and "pH-buffer management unit" each refer to a system measuring the pH and/or buffer concentration of a dialysate or fluid within the system.

The terms "potassium management system" and "potassium management unit" each refers to a system measuring the potassium concentration of a dialysate or fluid within the system.

The terms "fluid characteristic management system" and "fluid characteristic management unit" each refers to a system measuring one of more of the fluid characteristics such as pH, potassium concentration, sodium concentration, among others.

The term "pump" refers to any device that causes the movement of fluids or gases by the application of suction or pressure.

A "reconstitution system" in one use, is a system that rebalances the dialysate in the system to ensure it contains the appropriate amount of electrolytes and buffer.

A "semipermeable membrane", also termed a "selectively permeable membrane", a "partially permeable membrane" or a "differentially permeable membrane", is a membrane that will allow certain molecules or ions to pass through it by diffusion and occasionally specialized "facilitated diffusion". The rate of passage depends on the pressure, concentration, and temperature of the molecules or solutes on either side, as well as the permeability of the membrane to each solute. The term "semi-permeable membrane" can also refer to a material that inhibits the passage of larger molecular weight components of a solution while allowing passage of other components of a solution having a smaller molecular weight.

The term "static mixer" refers to a device that mixes two or more component materials in a fluid solution without requiring the use of moving parts.

"Thermal conductivity" (often denoted k, λ, or κ) is the property of a material, fluid, or gas to conduct heat. It is evaluated primarily in terms of Fourier's Law for heat conduction. Heat transfer across materials of high thermal conductivity occurs at a higher rate than across materials of low thermal conductivity.

The term "acid reacted fluid" refers to a fluid that has been reacted with an acid.

The term "base reacted fluid" refers to a fluid that has been reacted with a base.

The term "electrical conductivity" refers to the electrical conductance of a solution.

The term "measurement chamber" refers to a chamber where a measurement with a sensor is performed. The sensor may include a pressure sensor, electrical conductivity sensor or a thermal conductivity sensor.

The term "pressure transducer" refers to a device for measuring the pressure of a gas or liquid in a vessel or container. The term "pressure transducer" can be used interchangeably with the terms "pressure meter" and "pressure sensor."

The term "bicarbonate buffer concentrate" refers to a bicarbonate ($HCO_3^-$) buffer component composition at a higher concentration than found at normal physiological levels that can be used to for instants to readjusted the pH of the dialysate (see also definition of bicarbonate buffer component relating to its use).

The term "bicarbonate cartridge" refers to a container that can be a stand-alone container or alternatively can be integrally formed with an apparatus for hemodialysis, hemodiafiltration, or hemofiltration. The bicarbonate cartridge can store a source of buffering material, such as sodium bicarbonate, and can be configured to interface with at least one other functional module found in systems for hemodialysis, hemodiafiltration, or hemofiltration. For example, the bicarbonate cartridge can contain at least one fluid pathway and include components such as conduits, valves, filters or fluid connection ports. The bicarbonate cartridge can be disposable or be consumable wherein the cartridge is recharged upon depletion. Specifically, the term "bicarbonate consumables container" refers to an object or apparatus having or holding a material in solid and/or solution form that is a source of bicarbonate, such as sodium bicarbonate, that is depleted during operation of the system. The object or apparatus may be single use, or may be replenished and used multiple times, for example, by refilling the object to replace the consumed material.

The term "bicarbonate feed" refers to fluid solution introduced into part of the dialysis or ultrafiltrate system. For example a "bicarbonate feed" is a conduit that contains a bicarbonate buffer concentrate that is used to readjust the pH of the dialysate.

The term "bidirectional pump" refers to a device configured to perform work on a fluid to cause the fluid to flow alternatively in either of two opposing directions.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The terms "bypass circuit" "bypass conduit," "bypass flow path," "bypass conduit flow path" and "bypass" refer to a component or collection of components configured or operable to create an alternate fluid pathway to convey a fluid around one or more other components of a fluid circuit such that at least a portion of the fluid does not contact or pass through the one or more other components. At times the term "shunt" may be used interchangeable with the term "bypass." When any of the above "bypass" terms listed in this paragraph are used in context as being part of a controlled compliant system, then the relevant referenced "bypass" has the proper characteristics as to operate within a controlled compliant system as defined herein.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The terms "conduit," "conduit" or "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "chronic kidney disease" (CKD) refers to a condition characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail to function at a sufficient level.

The term "container" as used herein is a receptacle that may be flexible or inflexible for holding fluid or solid, such as for example a spent dialysate fluid, or a sodium chloride or sodium bicarbonate solution or solid.

The terms "common container," "common cartridge," or "common reservoir," and the like refer to an object or apparatus that can hold more than one material; however, the time of holding more than one material may or may not necessarily be at the same time. The material(s) may be in solid and/or solution forms and may be held in separate compartments within the object or apparatus.

The term "common fluid inlet port" refers to an opening or aperture through which all fluid first passes to enter an object, apparatus or assembly.

The term "common fluid outlet port" refers to an opening or aperture through which all fluid passes to exit an object, apparatus or assembly.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The terms "component" and "components" refer to a part or element of a larger set or system. As used herein, a component may be an individual element, or it may itself be a grouping of components that are configured as a set, for example, as a cassette or a cleaning and/or disinfection manifold.

The term "comprising" includes, but is not limited to, whatever follows the word "comprising." Thus, use of the term indicates that the listed elements are required or mandatory but that other elements are optional and may or may not be present.

The term "concentrate pump" refers to a device that can perform work on a fluid solution to cause the fluid flow and can actively control the transfer of fluid volume such as an infusate or an acid concentrate, base concentrate, or buffer concentrate into a circuit.

The terms "concentrate flow channel," "concentrate flow loop," "concentrate stream," refer to a fluid line in which ion concentration is increased during electrodialysis.

The terms "conduit," "circuit," and "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

The term "consisting of" includes and is limited to whatever follows the phrase "consisting of:" Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "contact," "contacted," and "contacting" refers, in context, to (1) a coming together or touching of objects, fluids, or surfaces; (2) the state or condition of touching or of immediate proximity; (3) connection or interaction. For example, in reference to a "dialysate contacting a sorbent material" refers to dialysate that has come together, has touched, or is in immediate proximity to connect or interact with any material or material layer of a sorbent container, system or cartridge.

The term "container" as used herein is a receptacle that may be flexible or inflexible for holding fluid or solid, such as for example a spent dialysate fluid, or a sodium chloride or sodium bicarbonate solution or solid, or the like.

The term "control signals" refers to energy that is provided from one element of a system to another element of a system to convey information from one element to another or to cause an action. For example, a control signal can energize a valve actuator to cause a valve to open or close. In another example a switch on a valve can convey the open or close state of a valve to a controller.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is approximately 140 mEq/L. Normal blood sodium levels range from approximately 135 mEq/L to 145 mEq/L. The REDY system typically uses dialysate ranging from 120 mEq/L to 160 mEq/L. In certain embodiment, a "predetermined limit" or "predetermined concentration" of sodium values can be based off the common sodium levels for dialysate and normal blood sodium levels. "Normal" saline at 0/9% by weight and commonly used for priming dialyzers and extracorporeal circuits is 154 mEq/L.

The terms "dialysate flow loop," "dialysate flow path," and "dialysate conduit flow path" refers, in context, to a fluid pathway that conveys a dialysate and is configured to form at least part of a fluid circuit for hemodialysis, hemofiltration, hemodiafiltration or ultrafiltration.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," and generally "membrane," refer, in context, to a semi-permeable barrier selective to allow diffusion and convection of solutes of a specific range of molecular weights through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Diffusive permeability" is a property of a membrane describing permeation by diffusion. Diffusion is the process of solutes moving from an area of higher concentration to an area of lower concentration.

The term "downstream" refers to a direction in which a moving dialysate or other fluid moves within a conduit or flow path.

The term "effluent dialysate," as used herein describes the discharge or outflow after the dialysate has been used for dialysis.

The term "electrode" as used herein describes an electrical conductor used to make contact with a nonmetallic part of a circuit, such as electrical conductors used to contact the fluids of the invention (e.g. dialysate) and to measure the conductivity of the fluid.

The term "electrode" as used herein describes an electrical conductor used to make contact with a part of a fluid, a solid or solution. For example, electrical conductors can be used as electrodes to contact any fluid (e.g. dialysate) to measure the conductivity of the fluid or deliver or receive charge to the fluid. A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode" refers to a rod electrode with a small diameter. Other electrode and electrode head geometries can be considered.

The term "electrode array" refers to an array of one or more electrodes contained in an insulator substrate. The insulator substrate can be rigid or flexible and acts to isolate the electrodes from each other. A non-limiting example of an "electrode array" is a flex-circuit, which is a flexible circuit board containing electrodes.

The term "electrode head" refers to the portion of an electrode that is in physical contact with a fluid, that conductivity is to be measured from.

The terms "electrode rinse" and "electrode rinse solution" refer to any suitable solution such as sodium sulfate solution that prevents undesirable oxidation and flushes reactants from an electrode surface.

The terms "electrode rinse flow channel," "electrode rinse stream," and the like refer to a fluid line of an electrode rinse or "electrode rinse solution."

The term "electrode rinse reservoir" refers to a vessel or container for holding the electrode rinse or electrode rinse solution. The reservoir may have an inflexible or flexible volume capacity.

The term "electrodialysis" refers to an electrically driven membrane separation process capable of separating, purifying, and concentrating desired ions from aqueous solutions or solvents.

The term "electrodialysis cell" refers to an apparatus having alternating anion- and cation-exchange membranes that can perform electrodialysis using an electrical driving force between an anode and cathode housed at opposite ends of the cell. The cell consists of a dilute compartment fed by a dilute stream and a concentrate compartment fed by a concentrate stream. One or more electrodialysis cells can be multiply arranged to form an "electrodialysis stack."

The term "electrolyte" refers to an ion or ions dissolved in an aqueous medium, including but not limited to sodium, potassium, calcium, magnesium, acetate, bicarbonate, and chloride.

The terms "electrolyte source" and "electrolyte source" refer to a stored substance that provides one or more electrolytes.

The terms "equilibrated," "equilibrate," "to equilibrate," and the like, refer to a state where a concentration of a solute in a first fluid has become approximately equal to the concentration of that solute in the second fluid. However, the term equilibrated as used herein does not imply that the concentration of the solute in the first fluid and the second fluid have become equal. The term can also be used in reference to the process of one or more gases coming into equilibrium where the gases have equal pressures or between a liquid and a gas.

The term "equilibrated to the solute species concentration" refers to more specifically where a concentration of a particular solute species in a first fluid has become approximately equal to the concentration of that solute species in the second fluid. The concentration need not be exact.

The terms "evacuation volume," "priming volume" and "void volume" refer to the internal volume of a component or collection of components comprising a fluid flow path and are the volume of fluid that can be removed from the fluid flow path to empty the fluid flow path if it has been filled with fluid.

The term "extracorporeal," as used herein generally means situated or occurring outside the body.

The term "extracorporeal circuit" refers to a fluid pathway incorporating one or more components such as, but not limited to, conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

The term "feed solution" refers to a dialysate or ultrafiltrate fluid solution introduced into part of the dialysis or ultrafiltrate system. For example a "feed solution" can refer to a dialysate or ultrafiltrate fluid solution introduced to an electrodialysis cell.

The term "filtering media" refers to a material that can allow a fluid to pass through, but which inhibits passage of non-fluid substances that are larger than a predetermined size.

The terms "filtrate regeneration unit" and "filtrate regeneration system" refer to a system for removing certain electrolytes and waste species including urea from a filtrate produced using filtration.

The terms "filtrate regeneration circuit," "filtrate regeneration loop," and the like, refer to a flow path containing fluid resulting from filtration; for the removal of certain electrolytes and waste species including urea.

The term "filtration" refers to a process of separating solutes from a fluid, by passing the fluid through a filter medium across which certain solutes or suspensions cannot pass. Filtration is driven by the pressure difference across the membrane.

The term "first terminal end" of a flow path refers to one end of the flow path and "second terminal end" refers to another end of the flow path. Neither the "first terminal end" nor the "second terminal end" has any limitation on placement on an arterial or venous side.

The term "first terminal valve" refers to a valve substantially located at one end of a first fluid conduit without any requirement that the valve be place on an arterial or venous side. Similarly, the term "second terminal valve" refers to a valve substantially located at one end of a second fluid conduit and so on without any limitation on placement on an arterial or venous side.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that it recirculates, or passes the same position more than once as it moves through a flow loop. A flow loop may operate to cause fluid volume ingress to and fluid volume egress from the flow loop. The term "flow loop" and "flow path" often may be used interchangeably. Further types of flow paths may be further defined; for example, (1) a recirculation flow path, would be a flow path whose function is in whole or part is to recirculate fluid through the defined flow path; (2) a dialyzer recirculation flow path would be a flow path whose function is in whole or part is to recirculate fluid through the defined flow path having a dialyzer' (3) a controlled compliant flow path would be a flow path would be a flow path that is controlled compliant as defined herein. Any of the defined flow paths may be referred to numerically, as a first flow path, second, third flow path, or fourth flow path, and the like flow paths.

The term "flow path" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably.

The terms "flow restriction," "flow restriction device" and "flow restrictor" refer to an element or grouping of elements that resist the flow of fluid through the element or grouping of elements such that the fluid pressure within a flow stream that passes through the element or grouping of elements is greater upstream of the element or grouping of elements than downstream of the element or grouping of elements. A flow restrictor may be an active or passive device. Non-limiting examples of passive flow restriction devices are orifices, venturis, a narrowing, or a simple length of tubing with flow cross section that produces the desired pressure drop when the fluid flows through it, such tubing being essentially rigid or compliant. Non-limiting examples of active flow restrictors are pinch valves, gate valves and variable orifice valves.

The term "flow stream" refers to fluid moving along a flow path

The term "fluid balance control pump" refers to where a control pump is used to adjust the concentration or amount of a solute or fluid in the system. For example, a fluid balance control pump is used for selectively metering in or selectively metering out a designated fluid wherein the concentration or amount of a solute or fluid is adjusted.

The term "fluid characteristic" refers to any chemical or biological components that make up or can be found dissolved or suspended in the fluid or gas properties associated with the fluid; or to any physical property of the fluid including, but not limited to temperature, pressure, general or specific conductivities associated with the fluid or related gases.

The term "fluid communication" refers to the ability of fluid to move from one component or compartment to another within a system or the state of being connected, such that fluid can move by pressure differences from one portion that is connected to another portion.

The term "fluid port" refers to an aperture through which a liquid or gas can be conveyed.

The term "fluid port cap or plug" refers to a device that can be connected to a fluid port to prevent fluid from passing through the fluid port. A fluid cap or plug may be configured into an apparatus having multiple caps or plugs to prevent fluid from passing through multiple fluid ports when the apparatus is connected to the multiple fluid ports.

The term "flush reservoir" is used to describe a container that can accept or store fluid that is removed from the system during rinsing or cleaning of fluid pathways of the system, including draining the system after cleaning and/or disinfection has been completed.

The term "forward osmosis" refers to a filtration method using an osmotic pressure gradient wherein a permeate side of a membrane contains a "draw" solution which has a higher osmotic potential than a feed solution on the other side of the membrane. That higher osmotic potential in the "draw" solution drives the filtration process wherein fluid moves through the membrane and is filtered in the process to dilute the higher solute concentration fluid on the permeate side.

The term "gas port" refers to an aperture through which any gaseous form of matter can be conveyed.

"Gas phase pressure," also known as "vapor," is the equilibrium pressure from a liquid or a solid at a specific temperature. If the vapor is in contact with a liquid or solid phase, the two phases will be in a state of equilibrium.

"Hemodiafiltration" is a therapy that combines hemofiltration and hemodialysis.

"Hemofiltration" is a therapy in which blood is filtered across a semi-permeable membrane. Water and solutes are removed from the blood via pressure-driven convection across the membrane. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) observed in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (predilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. Water and solutes are also transferred by convection across a pressure gradient that may exist across the dialysis membrane. The dialysate employed during hemodialysis has soluble ions such as sodium, calcium and potassium ions and is not pure water. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates.

The term "hemofilter" refers to a apparatus (or may refer to a filter) used in hemofiltration. A hemofilter apparatus can be connected to an extracorporeal circuit and configured to operate with a semipermeable membrane that separates at least a portion of the fluid volume from blood to produce a filtrate fluid.

The term "horizontal to a central axis" refers to a relative position of components such as sensors that can be placed in a plane having portions generally horizontal to the central axis.

The term "hydrophobic membrane" refers to a semipermeable porous material that may allow gas phases of matter to pass through, but which substantially resists the flow of water through the material due to the surface interaction between the water and the hydrophobic material.

The terms "hydrophobic vent" and "hydrophobic vent membrane" refer to a porous material layer or covering that can resist the passage of a liquid such as water through the pores while allowing the passage of a gas. The pores may also be of a sufficiently small size to substantially prevent the passage of microorganisms.

"Hemodiafiltration" is a therapy that combines hemofiltration and hemodialysis.

The term "perpendicular to a central axis" refers to the position of components, e.g. sensors that can be placed in a plane having portions generally perpendicular to the central axis.

The term "in contact" as referred to herein denotes (a) a coming together or touching, as of objects or surfaces; or (b) the state or condition of touching or of being in immediate proximity. "In contact" also includes fluids that are "in fluid communication with" with a solid, such as for example, a fluid, like a dialysate, in contact with a material layer of a sorbent cartridge, or a fluid in contact with a sensor.

The term "impedance meter" refers to a device for measuring the opposition of an object or structure to an alternating current.

The term "impurity species" refers to solutes in the blood that are in too high of a concentration in the blood from standard ranges known in the art or that are solutes that have resulted from metabolism to generate a non-healthy component now residing in the blood. An "impurity species" is one which is also regarded as a "waste species," or "waste products".

The term "ion selective electrode" refers to electrodes coated with a material that only allows certain ions to pass through. An "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The terms "infusate container" and "infusate reservoir" refer to a vessel, which can be substantially inflexible or non-flexible for holding a solution of one or more salts for the adjustment of the composition of a dialysate.

The term "infusate solution" refers to a solution of one or more salts for the adjustment of the composition of a dialysate, such as salts of calcium, magnesium, potassium, and glucose.

The term "infusate system" refers to a system that incorporates at least one fluid pathway including components such as conduits, valves, pumps or fluid connection ports, an infusate container or a controller configured to add an infusate solution to the dialysate.

The term "interchangeable bicarbonate cartridge" refers to a bicarbonate cartridge that can be configured for removal and replacement with a like bicarbonate cartridge. Interchangeable bicarbonate cartridges can be single use disposable, or re-fillable, re-usable containers.

The term "interchangeable sodium chloride cartridge" refers to a sodium chloride cartridge that can be configured for removal and replacement with a like sodium chloride cartridge. Interchangeable sodium chloride cartridges can be single use disposable, or re-fillable, re-usable containers.

The terms "introduce" and "introducing" refer to causing a substance to become present where it was not present, or to cause the amount or concentration of a substance to be increased.

The term "ion-exchange material" refers to any type of resin or material that can exchange one type of ion for another. The "ion-exchange material" can include anion and cation exchange materials. In one specific case, the term can refer to the removal of ions such as potassium, magnesium, sodium, phosphate and calcium in exchange for other ions such as potassium, sodium, acetate, hydrogen and/or hydroxide.

An "ion-exchange resin" or "ion-exchange polymer" is an insoluble matrix (or support structure) that can be in the form of small (1-2 mm diameter) beads, fabricated from an organic polymer substrate. The material has a developed structure of pores on the surface of which are sites with easily trapped and released ions. The trapping of ions takes place only with simultaneous releasing of other ions; thus the process is called ion-exchange. There are multiple different types of ion-exchange resin which are fabricated to selectively prefer one or several different types of ions. In one specific case, the term can refer to the removal of ions such as potassium, magnesium, sodium, phosphate and calcium in exchange for other ions such as potassium, sodium, acetate, hydrogen and/or hydroxide.

The term "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The term "junction" refers to a common point of connection between two or more flow paths or conduits that allows a liquid and/or a gas to move from one pathway or conduit to another. A junction may be a reversible connection that can be separated when transfer of a liquid and/or gas between the flow paths or conduits is not needed.

The term "kidney replacement therapy" as used herein describes the use of a provided system to replace, supplement, or augment the function of a patient with impaired kidney function, such as would occur for a patient with Chronic Kidney Disease. Examples of kidney replacement therapy would include dialysis, hemofiltration, hemodialysis, hemodiafiltration, peritoneal dialysis, and the like.

The terms "luer connector" and "luer adapter" refer to adapters or connectors conforming to International Standards Organization (ISO) standards 594-2.

The term "manifold" refers to a collection of one or more fluid pathways that are formed within a single unit or subassembly. Many types of manifolds can be used, e.g. a cleaning and/or disinfecting manifold is used to clean or disinfect the defined flow loop when the flow loop is connected to the cleaning and/or disinfecting manifold.

The term "material layer" refers to the layers of materials found in a sorbent cartridge. The material layers in a sorbent cartridge may have one or more layers selected from a urease-containing material, alumina, zirconium phosphate, zirconium oxide, and activated carbon.

The term "memory" refers to a device for recording digital information that can be accessed by a microprocessor, such as RAM, Dynamic RAM, microprocessor cache, FLASH memory, or memory card.

The term "mesh electrode" refers to an electrode in the shape of a mesh, where a mesh consists of a planar structure with openings. The mesh can be made from; overlapping wires or strips, a sheet machined or manufactured to contain holes or openings, or a sheet with a permeable, porous structure. In all cases the mesh is manufactured from materials that result in electrodes, such as titanium, platinum, stainless steel, and iridium. In the case of an electrode mesh consisting of overlapping wires or strips, certain wires or strips can be isolated from other wires or strips with an insulator material in order to apply one polarity to certain wires or strips and the opposite polarity to other wires or strips.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "mid-weight uremic wastes" refers to uremic wastes that can pass through a dialysis membrane and have a molecular weight less than about 66,000 g/mol and greater than about 1000 g/mol. An example of a middle molecule is beta-2 microglobulin.

The term "mixing chamber" refers to a chamber or vessel, with one or more inlet and outlet fluid streams, that provides mixing between the fluid streams entering the chamber.

The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow loop in a controlled compliant system.

A multiplexer" or "mux" is an electronic device that selects one of several analog or digital input signals and forwards the selected input into a single line.

The term "nitrogenous waste" refers to any non-polymeric nitrogen-containing organic compound originating from the blood of a patient. Nitrogenous waste includes urea and creatinine, which are both "waste species."

The term "one-way valve" refers to a device that allows flow to pass in one direction through the valve, but prevents or substantially resists flow through the valve in the opposite direction. Such devices can include devices commonly referred to as check valves "Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

The term "parallel or wound hollow fiber assembly" refers to any device that incorporates a porous or non-porous hollow fiber material that allows a gas to pass through the material wall of the hollow fibers, but resists the passage of a liquid through the material wall and is configured as multiple strands aligned in parallel or wrapped around a core. The liquid to be degassed may be conveyed through either the inside of the hollow fibers or around the outside of the hollow fibers. Optionally, a gas may be conveyed on the side of the material wall that is opposite the liquid to be degassed. Optionally, a vacuum may be applied on the side of the material wall that is opposite the liquid to be degassed.

A "patient" or "subject" is a member of any animal species, preferably a mammalian species, optionally a human. The subject can be an apparently healthy individual, an individual suffering from a disease, or an individual being treated for a disease.

The term "parallel to a central axis" refers to the position of components, e.g. sensors that can be placed in a plane having portions generally parallel to the central axis.

The terms "pathway," "conveyance pathway" and "flow path" refer to the route through which a fluid, such as dialysate or blood travels.

The term "patient fluid balance" refers to the amount or volume of fluid added to or removed from a subject undergoing a treatment.

The term "peristaltic pump" refers to a pump that operates by compression of a flexible conduit or tube through which the fluid to be pumped passes.

The term "perpendicular to a central axis" refers to the position of components, e.g. sensors that can be placed in a plane having portions generally perpendicular to the central axis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient.

The terms "portable system" and "wearable system" refers to a system in whole or in part having a mass and dimension to allow for transport by a single individual by carrying the system or wearing the system on the individual's body. The terms are to be interpreted broadly without any limitation as to size, weight, length of time carried, comfort, ease of use, and specific use by any person whether man, woman or child. The term is to be used in a general sense wherein one of ordinary skill will understand that portability as contemplated by the invention encompasses a wide range of weights, geometries, configurations and size.

The terms "physiologically compatible fluid" and "physiological compatible solution" refer to a fluid that can be safely introduced into the bloodstream of a living subject.

The term "plumbing," as used herein generally describes any system of valves, conduits, channels, and lines for supplying any of the fluids used in the invention.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pump" refers to any device that causes the movement of fluids or gases by the application of suction or pressure.

The term "pulsatile pump" refers to a pump where the pumped fluid undergoes periodic variation in velocity and/or pressure.

The terms "pump rate" and "volumetric pumping rate" refer to the volume of fluid that a pump conveys per unit of time.

The term "purified water" refers to water that has been physically processed to remove at least a portion of at least one impurity from the water.

The term "outlet stream" refers to a fluid stream exiting a chamber, vessel or cartridge.

The terms "reconstitute" and "reconstituting" refer to creating a solution by addition of a liquid to a dry material or to a solution of higher concentration to change the concentration level of the solution. A "reconstitution system" in one use, is a system that rebalances the dialysate in the system to ensure it contains the appropriate amount of electrolytes and buffer.

The term "shunt," as most often used herein describes a passage between channels, in the described filtration and purification systems, wherein the shunt diverts or permits flow from one pathway or region to another. An alternate meaning of "shunt" can refer to a pathway or passage by which a bodily fluid (such as blood) is diverted from one channel, circulatory path, or part to another. The term "bypass" can often be used interchangeably with the term "shunt."

The terms "replacement fluid" and "substitution fluid" refer to fluid that is delivered to the blood of a subject undergoing convective renal replacement therapies such as hemofiltration or hemodiafiltration in order to replace at least a portion of the fluid volume that is removed from the subject's blood when the blood is passed through a hemofilter or a dialyzer.

The term "segment" refers to a portion of the whole, such as a portion of a fluid flow path or a portion of a fluid circuit. A segment is not limited to a tube or conduit, and includes any grouping of elements that are described for a particular segment. Use of the term "segment," by itself, does not imply reversible or detachable connection to another segment. In any embodiment, a segment may be permanently connected to one or more other segments or removably or detachably connected to one or more segments.

The terms "selectively meter fluid in" and "selectively meter fluid out" generally refer to a process for controllably transferring fluids from one fluid compartment (e.g. a selected patient fluid volume, flow path, or reservoir) to another fluid compartment. One non-limiting example is where a control pump may transfer a defined fluid volume container, reservoirs, flow paths, conduit of the controlled compliant system. When fluid is moved from a reservoir into another part of the system, the process is referred to as "selectively metering fluid in" as related to that part of the system. Similarly, one non-limiting example of removing a defined volume of dialysate from a dialysate flow path in a controlled compliant system and storing the spent dialysate in a control reservoir can be referred to as "selectively metering-out" the fluid from the dialysate flow path.

The terms "semipermeable membrane," "selectively permeable membrane," "partially permeable membrane," and "differentially permeable membrane," refer to a membrane that will allow certain molecules or ions to pass through it by diffusion and occasionally specialized "facilitated diffusion". The rate of passage depends on the pressure, concentration, and temperature of the molecules or solutes on either side, as well as the permeability of the membrane to each solute. The term "semi-permeable membrane" can also refer to a material that inhibits the passage of larger molecular weight components of a solution while allowing passage of other components of a solution having a smaller molecular weight. For example, Dialyzer membranes come with different pore sizes. Those with smaller pore size are called "low-flux" and those with larger pore sizes are called "high-flux." Some larger molecules, such as beta-2-microglobulin, are not effectively removed with low-flux dialyzers. Because beta-2-microglobulin is a large molecule, with a molecular weight of about 11,600 daltons, it does not pass effectively through low-flux dialysis membranes.

The term "sensor," which can also be referred to as a "detector" in certain instances, as used herein can be a converter that measures a physical quantity of a matter in a solution, liquid or gas, and can convert it into a signal which can be read by an electronic instrument.

The term "sensor element" refers to a device or component of a system that detects or measures a physical property.

The term "solute" refers to a substance dissolved, suspended, or present in another substance, usually the component of a solution present in the lesser amount.

The terms "sorbent cartridge" and "sorbent container" refer to a cartridge containing one or more sorbent materials for removing specific solutes from solution, such as urea. "Sorbent cartridge" includes configurations where at least some of the materials contained in the cartridge do not act by mechanisms of adsorption or absorption.

The terms "sorbent regeneration," "sorbent regeneration system," "sorbent regeneration unit," "sorbent system," and the like, refer, in context, to devices that are part of a sorbent regenerated dialysate delivery system for hemodialysis functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "source of cations" refers a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid. Non-limiting examples include glucose, dextrose, acetic acid and citric acid.

The term "specified gas membrane permeability" refers to a determined rate at which a gas membrane will allow a gas to pass through the membrane from a first surface to a second surface, the rate being proportional to the difference in absolute pressure of the gas in proximity to the first side of the membrane and in proximity to the second side of the membrane.

The term "spent dialysate" refers to a dialysate that has been contacted with blood through a dialysis membrane and contains one or more impurity, or waste species, or waste substance, such as urea.

The term "static mixer" refers to a device that mixes two or more component materials in a fluid solution without requiring the use of moving parts.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

The term "total bicarbonate buffer concentration" refers to the total concentration of bicarbonate ($HCO_3^-$) ion and a conjugate acid of bicarbonate in a solution or composition.

A "therapy solution reservoir" refers to any container or reservoir that holds a physiological compatible fluid.

The terms "treating" and "treatment" refer to the management and care of a patient having a pathology or condition by administration of one or more therapy contemplated by the present invention. Treating also includes administering one or more methods of the present invention or using any of the systems, devices or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "uremic wastes" refers to a milieu of substances found in patients with end-stage renal disease, including urea, creatinine, beta-2-microglobulin.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, a hemodiafiltration, or a filtration process.

The terms "unbuffered sodium bicarbonate" or "solution of unbuffered sodium bicarbonate" refer to a sodium bicarbonate composition that is not buffered with a conjugate acid or base in any amount, proportion or pH adjustment.

The term "upstream" refers to a direction opposite to the direction of travel of a moving dialysate or other fluid within a conduit or flow path.

The term "urea sensor" refers to a device for measuring or allowing for the calculation of urea content of a solution. The "urea sensor" can include devices measuring urease breakdown of urea and measurement of the resulting ammonium concentration. The sensing methods can be based on any one of conductimetric, potentiometric, thermometric, magnetoinductic, optical methods, combinations thereof and other methods known to those of skill in the art.

The term "vacuum" refers to an action that results from application of a pressure that is less than atmospheric pressure, or negative to the reference fluid or gas.

The term "vent" as referred to in relationship to a gas, refers to permitting the escape of a gas from a defined portion of the system, such as, for example, as would be found in the degassing module.

The term "void volume" refers to a specific volume that can be occupied by a fluid in a defined space such as a dialysate circuit of the invention including all components contained therein.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "working dialysate solution" refers to a dialysate solution that is undergoing active circulation or movement through a system including conduits, pathways, dialyzers and cartridges.

Dialysis System

FIG. 1 is an example of a dialysis system comprising a blood path and a dialysate regeneration path separated by a dialyzer 20. The blood enters the dialyzer 20 through a flow line inlet 22 and exits through a flow line outlet 24. The dialysate regeneration circuit shown in FIG. 1 can have either a flow loop 46 that is controlled compliant, or a flow loop that does not display the controlled compliant properties as defined herein. In certain embodiments of the invention (not shown), the dialysis systems may also have a non-compliant volume as defined herein. The dialysate solution is recirculated with a dialysate pump 30 and allowed to flow through a sorbent system 32.

The sorbent system 32 includes components or materials that are capable of removing solutes from the dialysate including: urea, phosphate, calcium, magnesium, potassium, creatinine, uric acid, beta-2-microglobulin and sulfate. The sorbent system 32 may also contain components or materials that release or bind sodium during the process of removing solutes from the dialysate. In certain embodiments, the sorbent system 32 can be a sorbent cartridge containing activated carbon, urease, zirconium phosphate and hydrous zirconium oxide, and combinations thereof including mixtures of any one of the components similar to known sorbent cartridges used in the "REDY" system.

Blood circulating through the dialyzer 20 via an extracorporeal flow path exchanges waste components with dialysate circulating through the dialyzer 20 and dialysate flow path 46. Waste species including ions and uremic toxins, such as uric acid, creatinine, and β2-microglobin, and urea, diffuse from the blood to the dialysate within the dialyzer 20 via a semipermeable membrane contained therein. As such, the limited volume of dialysate within the dialysate flow path 46 can reach equilibrium within several minutes with the content of waste species in the blood without ongoing removal of waste species from the dialysate to maintain a concentration gradient of waste species between the blood and the dialysate within the dialysate flow path 46.

Regeneration of the dialysate within the dialysate flow path 46 can be achieved through contacting the dialysate with sorbents contained within the sorbent system 32. Examples of useful sorbent materials include the REDY sorbent system and U.S. Pat. Nos. 3,669,880; 3,989,622; 4,581,141; 4,460,555; 4,650,587; 3,850,835; 6,627,164; 6,818,196; and 7,566,432 and U.S. Patent Publications 2010/007838; 2010/0084330; and 2010/0078381 and International Patent Publication WO 2009/157877 A1, which are incorporated herein by reference. In some embodiments, the sorbent system 32 can contain one or more materials selected from the group consisting of: 1) a urease-containing material, where urease is an enzyme that catalyzes the conversion of urea to ammonium ions and carbon dioxide; 2) a zirconium phosphate (ZrP) material that has the capacity to act as a cation exchanger by absorbing a large quantity of ammonium ions in exchange for sodium and hydrogen ions; 3) a zirconium oxide material (ZrO), which acts as an anion exchanger by exchanging phosphate for acetate; and 4) an activated carbon material that has a surface area for adsorption of wide range of impurities including metal ions and uremic toxins, such as uric acid, creatinine, and β2-microglobin. In some embodiments, the zirconium phosphate material can be replaced with a magnesium phosphate material. The term zirconium oxide is used interchangeably with the term hydrous zirconium oxide.

The principal waste species removed during treatment of a patient is urea that accumulates in the blood of individuals with various degrees of kidney disease or impairment. Since urea is an electrically neutral species, the sorbent system 32 can convert urea to a charged ammonium species that can then be removed from the dialysate before the dialysate exits the regeneration unit 32. However, in order to maintain electrical neutrality, the removal of charged ammonium species is matched by exchange with another charged species, which can be sodium ion and/or hydrogen ion in certain embodiments. Further, carbonate ion and/or $CO_2$ is also a product of urease activity. Dialysates typically include a bicarbonate buffer; however, the generation of hydrogen ions and carbonate ions by the sorbent system 32 can affect the pH and total bicarbonate buffer composition of the dialysate.

The components forming the dialysate flow loop of the invention can have a controlled compliant volume wherein the dialysate flow loop further incorporates a control or ultrafiltration pump that can be operated bi-directionally to cause the net movement of fluid from an extracorporeal side of the dialyzer into the dialysis flow loop or to cause net movement of fluid from the dialysate flow loop into the extracorporeal side of the dialyzer. In particular, a control or ultrafiltration pump is operated in the efflux direction to cause the movement of fluid from the extracorporeal side of the dialyzer into the dialysis flow loop and in the influx direction to cause the movement of fluid from the dialysis flow loop into the extracorporeal side of the dialyzer. The action of typical pumps contemplated by the invention function by expanding or contracting a space wherein any suitable type of pump can be used in the present invention.

In certain embodiments, operation of the control or ultrafiltration pump in the influx direction can be substituted with operation of the infusate pump to drive liquid from the infusate reservoir into the dialysis flow loop and subsequently cause movement of fluid from the dialysis flow loop to the extracorporeal side of the dialyzer. The control or ultrafiltration pump can also be used for the movement of fluid in the opposite direction across the dialyzer into the dialysis flow loop. It is noted that the infusate reservoir or ultrafiltrate reservoir can allow the system to adjust the patient fluid volume by withdrawing fluid and storing the desired amount in the respective reservoir and/or by providing rebalanced fluids to the patient and removing waste products. For example, the fluid stored in a control reservoir attached to the dialysate circuit can be used to store a volume of fluid equal to the ultrafiltrate volume removed from the patient during ultrafiltration (UF). Alternatively, the fluid stored in the control reservoir can be an infusate delivered to the patient. In certain embodiments, the delivered fluid can contain a therapeutic component deliverable across the dialyzer and into the patient's bloodstream. Additionally, the volume of the dialysate flow loop can be actively controlled by the user or a programmed controller.

The control or ultrafiltration pump allows for fluid to move from the dialysate flow loop to the extracorporeal side without creating a vacuum, wherein the operation of the control pump is controlled as described herein. Likewise, the control pump allows for fluid to move from the extracorporeal side and hence the patient's body, via the action of the control pump. Movement of fluid between the extracorporeal side of the dialyzer and the dialysate flow loop can be accurately controlled and metered using the removed fluid in certain embodiments. In other embodiments, the removed fluid can be transferred back to the patient through the dialysate flow loop using the ultrafiltrate stored in ultrafiltration reservoir. In some embodiments, the ultrafiltration reservoir can be prefilled with water, dialysate or other fluid for addition to the dialysate flow loop and/or for use or treatment within the sodium control system.

As such, some embodiments have a controlled compliant dialysate flow loop that can be accurately controlled to precisely remove or add fluid to the extracorporeal side of the dialyzer. Due to the substantially inflexible void volume of the conduits, the dialysate regeneration unit and other components of the dialysate flow loop, the net movement of fluid over any time interval across the dialysate membrane within the dialyzer can be accurately controlled by creating a means to accurately introduce or remove fluid from the patient. This capability can further be used to enhance the convective clearance of the system for uremic impurities while controlling the net fluid removed from the patient, for example, creating periods of fluid movement across the membrane with occasional reversal of direction. In certain embodiments, an ultrafiltrate can be used as described herein. However, the present invention is not limited to a controlled compliant flow path. As such, the dialysate flow loop in certain embodiments is not a controlled compliant flow path and may include one or more open reservoir for storing or accumulating dialysate.

In certain embodiments, a control pump can be a peristaltic pump, a volumetric metering pump, diaphragm pump, or a syringe style pump. Hence, the dialysate flow loop has a substantially inflexible volume except for controlled changes in volume modulated by the control or ultrafiltration pump, the infusion pump and optionally any other pumps that add fluid to the dialysate flow loop. The contents of U.S. patent application Ser. No. 13/565,733 filed on Aug. 2, 2012 are incorporated herein by references in their totality.

In certain embodiments, the urea entering the sorbent system 32 will break down into ammonium carbonate. A portion of the carbonate ions will convert to carbon dioxide or bicarbonate depending on characteristics of the sorbent system 32. In certain embodiments the ammonium carbonate will pass through a cation-exchange resin, such as ZrP, which will remove ammonium in exchange for hydrogen ions and sodium ions. The amount of hydrogen and sodium ions released will influence the dialysate solution pH and ultimately the concentration of carbon dioxide and bicarbonate in solution. Determining the concentration of bicarbonate and the pH allows adjustment of the pH and buffer concentration in order to achieve a specific therapeutic goal related to a patient's acid-base balance. Methods to measure the pH and buffer concentration are described below.

After passing through the sorbent system 32, the dialysate flows through a degasser 33. The degasser 33 can remove gasses dissolved in solution as well as non-dissolved gasses from the dialysate fluid, such as carbon dioxide, oxygen and nitrogen. The degasser 33 can contain a chamber containing a hydrophobic membrane allowing release of gas, also known as a membrane contacting degasser. The hydrophobic membrane can contain polytetrafluoroethylene (PTFE), polypropylene, or other suitable materials that allow for gas removal, but retard water intrusion. The degasser 33 may function passively or actively. Passive degassing involves passing the dialysate through a degassing chamber containing a hydrophobic membrane and allowing gas to escape based on the uncontrolled environmental conditions on the non-dialysate side of the hydrophobic membrane. Active degassing involves passing the dialysate through a degassing chamber containing a hydrophobic membrane and actively controlling the environmental conditions on the non-dialysate side of the membrane. For example, the non-dialysate side of the hydrophobic membrane can be placed under reduced pressure to drive gas removal from the dialysate. The reduced pressure could be controlled to influence the rate of gas removal. Active degassing could also involve passing a stripping gas along the non-dialysate side of the hydrophobic membrane. The stripping gas can be the atmosphere contained on the exterior of the dialysis system, or be supplied from a gas cylinder of nitrogen, argon, helium, or other suitable gas. The flow rate of the stripping gas can be controlled to influence the rate of gas removal. The rate of gas removal could also be monitored with a flow meter in order to perform closed-loop control of the active degasser. The degasser 33 can also include a chamber that promotes gas nucleation and subsequent removal from the dialysate. For example, the degassing chamber can have modified surfaces, such as increased surface roughness or micropatterns, to increase surface area and thereby promote gas removal. The degassing chamber can also contain materials that have high-surface area, such as boiling stones or surface modified particles. Gas nucleation promoters can be used with both active and passive degassing methods. An example of commercially available boiling stones is PTFE boiling stones sold by Sigma-Aldrich (St. Louis, Mo.). An example of a commercially available membrane contacting degasser is the Liqui-Cell Minimodule™ sold by Membrana (Charlotte, N.C.).

After passing through the degasser 33 the dialysate flows through a pH-buffer measurement system 38 and/or a by-pass loop 36, regulated by a by-pass regulator 34. The by-pass regulator 34 controls the amount of dialysate that passes through the pH-buffer measurement system 38. The by-pass regulator 34 could include a pinch valve, on/off valve, or a valve with a range of open conditions such as a needle valve. The by-pass loop 36 could also include a 3-way valve (not shown) to act as a by-pass regulator. The pH-buffer measurement system 38 can measure the pH and buffer concentration of the dialysate. The pH-buffer measurement system 38 and by-pass loop 36 may be placed anywhere along flow path 46, but preferably immediately after the sorbent system 32. Because the sorbent system 32 removes waste species from the dialysate, including urea, and electrolytes, such as potassium ions, magnesium ions and calcium ions, the pH-buffer measurement system 38 located after the sorbent system 32 will not be influenced by the concentration of potassium, magnesium or calcium ions. Therefore, the accuracy of the pH-buffer measurement system 38 is increased.

After passing through the pH-buffer measurement system 38 or by-pass loop 36 the dialysate flow passes a conductivity sensor 40. The conductivity sensor 40 may also be connected anywhere along the dialysate flow path 46. The conductivity sensor 40 measures the conductivity of the dialysate solution, which is a measure of the total sodium concentration wherein sodium is the major conductive species in the dialysate before and after the sorbent system 32. The conductivity sensor 40 can be used for safety purposes to determine if the sodium concentration of the dialysate is at an acceptable level for the patient. In one mode of operation, as shown in FIG. 1, after the conductivity sensor the dialysate flows through a reconstitution system 43 having an infusate pump 42 and an infusate reservoir 44. The reconstitution system 43 rebalances the dialysate to ensure it contains the appropriate amount of electrolytes and buffer. The infusate reservoir 44 can contain multiple reservoirs each containing specific compounds or solutions (not shown). For example, the infusate reservoir 44 can include a reservoir containing a concentrated electrolyte solution such as calcium acetate, magnesium acetate and potassium acetate. The infusate reservoir 44 can also contain an additional reservoir having a concentrated buffer solution such as sodium bicarbonate (not shown). Moreover, in certain embodiments multiple reconstitution systems 43 can be used with the dialysis system shown in FIG. 1 as needed to provide an infusate.

Regenerated dialysate 25 passes through the dialyzer 20 and exits the dialyzer 20 as waste or spent dialysate 23. The waste dialysate exits the dialyzer and enters a portion of the conduit 23, and then flows by an ultrafiltration unit that has an ultrafiltration or control pump 28 and an ultrafiltration reservoir 26. The ultrafiltration pump 28 can remove fluid from the dialysate flow path 46 and, because of the dialysate flow path's 46 substantially inflexible volume or controlled compliant properties as described herein, fluid is drawn across dialyzer 20 from the blood. The ultrafiltration system can remove ultrafiltrate from the patient and remove any fluid volume added in along the dialysate flow path 46, such as fluid from the reconstitution system 43. The fluid removed by ultrafiltrate pump 28 is collected in the ultrafiltrate reservoir 26.

In certain embodiments, the components of the dialysate flow path 46 have a controlled compliant volume to form a controlled compliant dialysate path. As such, fluid is blocked from passively flowing from the extracorporeal flow path or blood path to the dialysate flow path 46 due to the controlled compliant volume of the dialysate flow path 46. Fluid is prevented from passively flowing between the flow path 46 to the extracorporeal flow path via the dialyzer 20 since such a movement of fluid will leave a vacuum in the flow path 46 or require the flow path 46 to expand. Since the dialyzer can be a high-flux type that readily allows for the passage of water, there can be some fluid flux back and forth across the dialyzer membrane due to the pressure differential on the blood and dialysate sides of the membrane. This is a localized phenomenon due to the low pressure required to move solution across the membrane and is called backfiltration, however, this results in no net fluid gain or loss by the patient.

In any embodiment of the invention, the components forming the dialysate flow path 46 can have a controlled compliant volume such that the dialysate flow path 46 further incorporates a control or ultrafiltration pump 28 that can be operated bi-directionally to cause the movement of fluid from an extracorporeal side of the dialyzer 20 into the dialysis flow path 46 or to cause net movement of fluid from the dialysate flow path 46 into the extracorporeal side of the dialyzer 20. Specifically, the control or ultrafiltration pump 28 can be operated in the efflux direction to cause the movement of fluid from the extracorporeal side of the dialyzer 20 into the dialysis flow path 46 and in the influx direction to cause the movement of fluid from the dialysis flow path 46 into the extracorporeal side of the dialyzer 20. The action of typical pumps contemplated by the invention can function by expanding or contracting a space wherein any suitable type can be used in the present invention.

In certain embodiments, operation of the control or ultrafiltration pump 28 in the influx direction can be substituted with operation of the infusate pump 42 to drive liquid from the infusate reservoir 44 into the dialysate flow path 46 and subsequently cause movement of fluid from the dialysis flow path 46 to the extracorporeal side of the dialyzer 20. The control or ultrafiltration pump 28 can also be used for the movement of fluid in the opposite direction across the dialyzer 20 into the dialysate flow path 46. It is noted that the infusate reservoir 44 or ultrafiltrate reservoir 26 can allow the system to adjust the patient fluid volume by withdrawing fluid and storing the desired amount in the respective reservoir and/or by providing rebalanced fluids to the patient and removing waste products. For example, the fluid stored in a control reservoir attached to the dialysate flow path can be used to store a volume of fluid equal to the ultrafiltrate volume removed from the patient during ultrafiltration (UF). Alternatively, the fluid stored in the control reservoir can be an infusate delivered to the patient. In certain embodiments, the delivered fluid can contain a therapeutic component deliverable across the dialyzer 20 and into the patient's bloodstream. Additionally, the volume of the dialysate flow path 46 can be actively controlled by the user or a programmed controller.

The control or ultrafiltration pump 28 allows for fluid to move from the dialysate flow path 46 to the extracorporeal side without creating a vacuum, wherein the operation of the control pump 28 is controlled as described herein. Likewise, the control pump 28 allows for fluid to move from the extracorporeal side, and hence from/to the patient's body via the action of the control pump 28 as described herein. Movement of fluid between the extracorporeal side of the dialyzer 20 and the dialysate flow path 46 can be accurately controlled and metered using the removed fluid in certain embodiments. In other embodiments, the removed fluid can be transferred back to the patient through dialysate flow path 46 using ultrafiltrate stored in the ultrafiltrate reservoir 26.

As such, some embodiments have a controlled compliant dialysate flow path 46 that can be accurately controlled to precisely remove or add fluid to the extracorporeal side of the dialyzer 20. Due to the substantially inflexible void volume of the conduits, the sorbent system 32 and other components of the dialysate flow path 46, the net movement of fluid over any time interval across the dialysate membrane within the dialyzer 20 can be accurately controlled by creating a means to accurately introduce or remove fluid from the patient. This capability can further be used to enhance the convective clearance of the system for uremic impurities while controlling the net fluid removed from the patient, for example, creating periods of fluid movement across the membrane with occasional reversal of direction to remove waste species by solvent drag. However, the present invention is not limited to a controlled compliant flow path. As such, the dialysate flow path 46 in certain embodiments is not a controlled compliant flow path and may include one or more open reservoirs for storing or accumulating dialysate.

In certain embodiments, a control or ultrafiltration pump 28 can be a peristaltic pump, a volumetric metering pump, diaphragm pump, or a syringe style pump. Hence, the dialysate flow path 46 has a substantially inflexible volume that can deliver controlled changes in fluid to the patient modulated by the control or ultrafiltration pump 28, or the infusate pump 42 or optionally any other pump(s) that add or remove fluid to and from the dialysate flow path 46. The contents of U.S. patent application Ser. No. 13/565,733 filed on Aug. 2, 2012 are incorporated herein by reference in their totality.

In certain embodiments, the dialysate flow path 46 has a void volume from about 0.15 L to about 0.5 L. In other embodiments, the dialysate flow path 46 has a void volume from about 0.2 L to about 0.4 L or from 0.2 L to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 L to about 5 L, and micro-volumes from as small as 0.1 L to about 0.5 L such as 0.1 L to 0.2 L, 0.1 L to 0.3 L, 0.1 L to 0.4 L, 0.2 L to 0.3 L, 0.3 L to 0.4 L, or 0.3 L to 0.5 L are contemplated by the invention.

Configuration of pH-Buffer Measurement System

Figure 2:
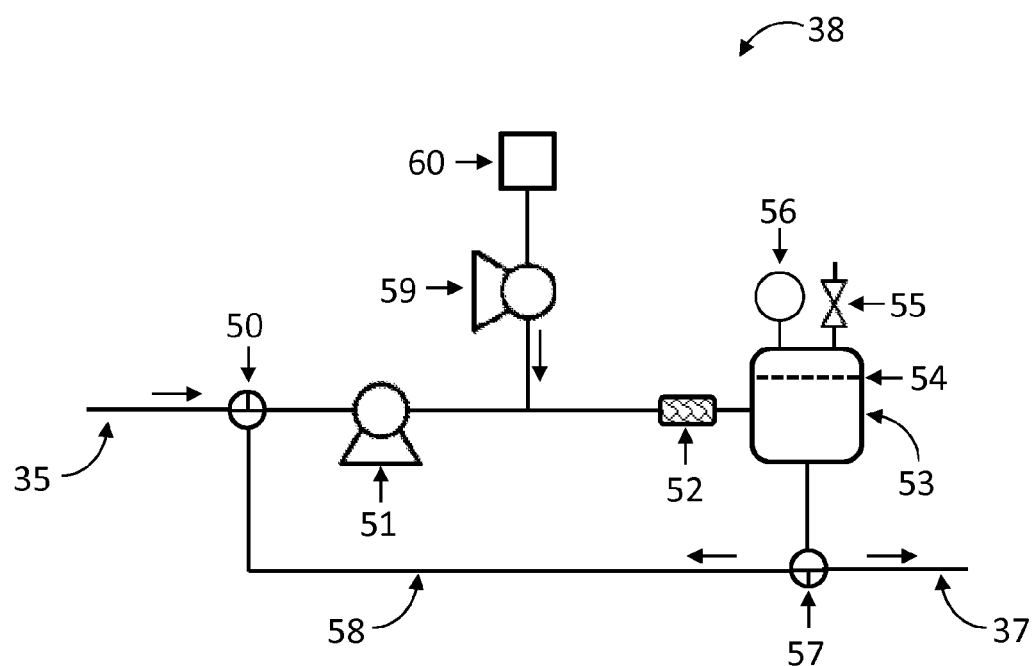
FIG. 2 is a pH-buffer measurement system utilizing a pressure sensor and an acid feed.

FIG. 2 is flow diagram of a pH-buffer measurement system utilizing an acid feed and a pressure sensor. Dialysate 35 exiting the degasser 33 of FIGS. 1, 6, 7, 8 and 9 flows into the pH-buffer measurement system 38 through the three-way valve 50. The volume of dialysate 35 drawn into the pH-buffer measurement system 38 is determined by fluid pump 51. Fluid pump 51 may include peristaltic, roller, gear, piston, or other pump types known to those of skill in the art for accurately metering fluids into a flow path. The dialysate flows through pump 51 and passes an acid feed stream consisting of an acid feed pump 59 and an acid reservoir 60. Acid ($H^+$) is metered into the flow path to drive the conversion of bicarbonate ($HCO_3^-$) present in the dialysate to carbon dioxide ($CO_2$) by reaction 1, shown below:

$$HCO_3^- + CO_2 + H^+ \rightarrow 2CO_2 + H_2O \qquad \text{Reaction 1.}$$

The acid is added in excess in a predetermined amount to ensure complete conversion of the bicarbonate. Example acids that can be utilized include acetic acid, citric acid, hydrochloric acid, phosphoric acid or other organic or inorganic acids known to those of skill in the art. Preferably the acid is dissolved in water to form an acidic aqueous solution of known molarity. Molarities can be in the range from 0.0001 to 1.0 molar. The acid feed stream can be introduced for a fixed period of time through the acid feed pump 59 and then shut off. The volume of acid added to the flow path can vary depending on the acid used and its molarity. Preferably the volume of acid introduced per measurement will be 10 milliliters or less. After flowing past the acid feed stream, the solution flows through a static mixer 52 to enhance the mixing between the acid solution and the dialysate. Flow continues into a measurement chamber 53 that includes a gas permeable membrane 54 of the type described above for the degasser. The measurement chamber 53 can also have an air-gap above the gas permeable membrane 54 that is in fluid communication with a pressure transducer 56 and a vent valve 55. The pressure transducer 56 measures pressure of the gas phase above the liquid dialysate and can include for example model PX309-030AI sold by Omega Engineering (Stamford, Conn.). Other types of known pressure transducers suitable for use in the present invention can be used. The vent valve 55 allows gas to escape from the measurement chamber 53. The solution contained in the measurement chamber 53 can flow out of the chamber through three-way valve 57 and be directed out of the pH-buffer measurement system 38 or recirculated within the system. After a sufficient amount of acid is introduced and the acid feed pump 59 is turned off, the three-way valves 50 and 57 are positioned to allow recirculation through the static mixer 52 and measurement chamber 53, by pump 51. Recirculation is performed to allow complete reaction between the bicarbonate and the acid to form carbon dioxide and to allow the pressure reading to stabilize. The pressure reading relates to the amount of carbon dioxide contained in the solution by Henry's law, which states that the partial pressure of a gas above a liquid is proportional to the concentration of the gas dissolved in the liquid. The proportionality constant is called the Henry's law constant and is dependent on temperature, gas type, atmospheric pressure and solution properties like solute composition and concentration. Certain parameters of the dialysate solution 35 can be measured to help determine the Henry's law constant including the electrical conductivity, which is related to the composition of ions in solution, and solution temperature. Ideally, the pH-buffer measurement system 38 is placed after the sorbent system 32 and degasser 33 as shown in FIGS. 1, 6, 7, 8 and 9. In that case the dialysate 35 entering the pH-buffer measurement system 38 will predominately contain sodium ions, chloride ions, acetate, bicarbonate, glucose and carbon dioxide. However, the pH-buffer measurement system 38 can be placed at any point along the dialysate flow path 46. The major species will be sodium ions, typically between 100 and 160 millimoles per liter. Therefore, the measurement of conductivity with the conductivity sensor 40 will relate to the sodium ion concentration and can be used along with temperature and the measure of atmospheric pressure with an absolute pressure sensor to determine the Henry's law constant for the solution during measurement.

The pH-buffer measurement system of FIG. 2 can be used to measure the concentration of bicarbonate in the dialysate. By measuring the carbon dioxide in the dialysate before and after complete conversion with acid, the concentration of bicarbonate in the dialysate can be determined and will be related to the pressure difference measured between the acidified dialysate and non-acidified dialysate. For example, in certain cases the dialysate can be recirculated through fluid flow path 58 and the pressure measured with pressure sensor 56 to determine the total pressure of gases in equilibrium with the dialysate, which includes carbon dioxide and other gases. The dialysate can then be acidified, as described above, to convert all of the bicarbonate to carbon dioxide and the total pressure of gases in equilibrium with the dialysate can be measured with pressure sensor 56. The total pressure includes the initial carbon dioxide, carbon dioxide from bicarbonate and other gases in the dialysate. The concentration of carbon dioxide resulting from bicarbonate can be determined by the pressure difference between the dialysate and acidified dialysate and the use of Henry's law. The pressure difference between the dialysate and acidified dialysate equals the partial pressure of carbon dioxide resulting from bicarbonate. The partial pressure value can be used to determine the concentration of carbon dioxide in the dialysate resulting from bicarbonate using Henry's law, and stoichiometry can be used to back calculate the bicarbonate concentration originally present in the dialysate. A control system can be employed to perform the calculations necessary to determine the concentrations described above.

In certain embodiments, the volume of the pH-buffer measurement system 38 can be small and can be less than 50 milliliters. Also, the amount of dialysate needed to perform a measurement can be less than 50 milliliters in certain embodiments. The time required to perform a measurement will be determined by the rate of reaction between the acid and the dialysate and the time required to reach a stable pressure measurement as the carbon dioxide equilibrates in the air-gap above the gas permeable membrane 54. In order to decrease the measurement time the recirculation rate, controlled by pump 51, can be increased. If the volume of the pH-buffer measurement system 38 is substantially smaller than the volume of the dialysate flow path 46, preferably less than 2% of the dialysate flow path 46 void volume, the acidified dialysate can be returned back to the dialysate flow path 46, without substantially affecting the pH or bicarbonate concentration of the dialysate. Also, between measurement of acidified dialysate and normal dialysate the pH-buffer measurement system 38 can be flushed with dialysate 35 entering the pH-buffer measurement system 38. If the volume and measurement time are sufficiently small, several measurements can be performed over a period of time and averaged to increase the accuracy of the calculated bicarbonate concentration.

The flow diagram for the pH-buffer measurement system 38 shown in FIG. 2 can be modified (not shown) to include two or more separate measurement chambers 53. In certain embodiments, a first measurement chamber can be used to measure the pressure of acidified dialysate and another measurement chamber can be used to measure the pressure of the dialysate. This configuration would allow the use of a single differential pressure sensor that could be in fluid communication with the gas phase of each measurement chamber. The use of a single differential pressure sensor can result in increased accuracy compared to performing separate measurements with a single pressure sensor and calculating the difference. Differential pressure sensors work by measuring the pressure difference between two fluid sources. A commercially available differential pressure sensor that can be used is PX409-005DDU5V sold by Omega Engineering (Stamford, Conn.). Other suitable pressure sensors known in the art can also be used.

Figure 3:
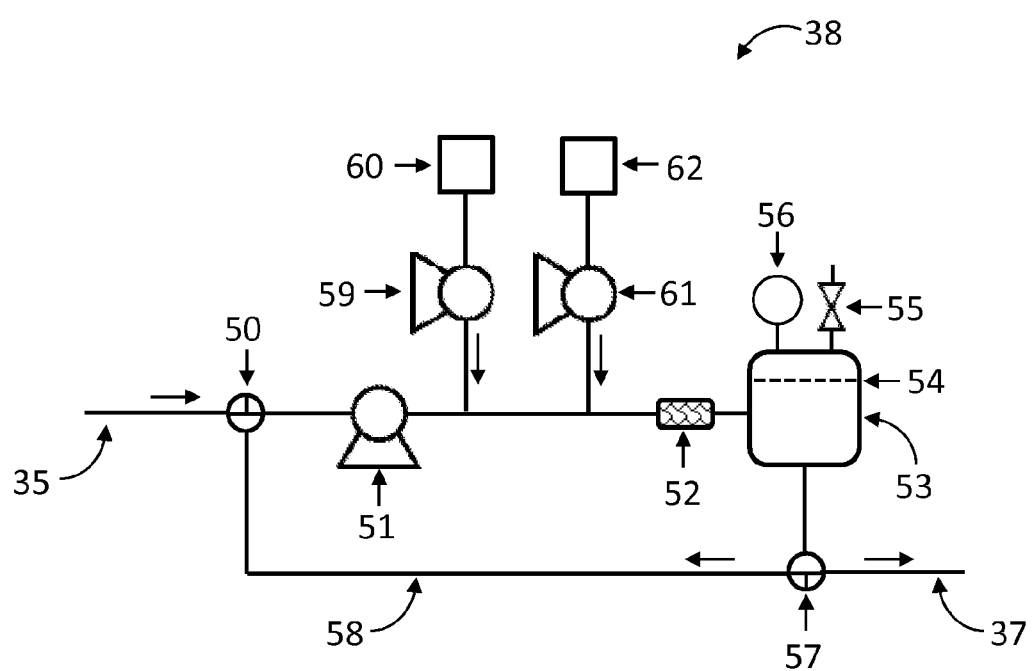
FIG. 3 is a pH-buffer measurement system utilizing a pressure sensor and an acid and base feed.

FIG. 3 is a flow diagram for a pH-buffer measurement system 38 that is capable of measuring the pH of the dialysate and the bicarbonate concentration. The presence of other gases contributing to the pressure measurement of the dialysate described above, make it difficult to determine the concentration of carbon dioxide in the dialysate. Therefore the pH-buffer measurement system shown in FIG. 3 includes a base feed pump 61 for providing a base and a base reservoir 62 containing the base. The base contained in the base reservoir 62 can include aqueous solutions of sodium hydroxide, potassium hydroxide or other suitable base solutions known to one of ordinary skill in the art. In other embodiments, the base can be in a solid form and be reconstituted with fluid in a mixing chamber or directly in the reservoir. In certain embodiments, the concentration of base required can be between 0.0001 molar and 1.0 molar or other values suitable for the intended use in the present system for taking measurements. The addition of base (OH$^-$) to the dialysate 35 entering the pH-buffer measurement system 38 will drive the reaction of carbon dioxide to bicarbonate as shown in reaction 2 below:

$$HCO_3^- + CO_2 + OH^- \rightarrow 2HCO_3^- \qquad \text{Reaction 2.}$$

Therefore, the measurement of pressure in the gas phase of the dialysate and the acid and base reacted dialysates, as described above, will allow the determination of the carbon dioxide and bicarbonate concentrations in the dialysate. Converting all of the carbon dioxide to bicarbonate will result in a pressure measurement resulting from residual gases in the dialysate only. The addition of base to the dialysate will not affect the level of residual gas. Therefore, the pressure difference between acidified dialysate and non-reacted dialysate can be used to determine the concentration of bicarbonate in the dialysate as described above. In the same manner the pressure difference between the dialysate and the base modified dialysate can be used to determine the concentration of carbon dioxide in the dialysate using the same methods described above. Once the bicarbonate and carbon dioxide concentration in the dialysate are known, the pH can be calculated using the Henderson-Hasselbalch equation:

where $_pCO_2$ (partial pressure of carbon dioxide (mmHg) and pH are measured. The $pK_a$ and $\alpha$ (solubility coefficient of carbon dioxide in dialysate (mmol-liter$^{-1}$-mmHg$^{-1}$) will be calculated for the dialysate solution at a given temperature. The temperature may be measured with a temperature sensor along the dialysate flow path 46. The $pK_a$ and $\alpha$ can be calculated by methods known to those skilled in the art. The partial pressure of carbon dioxide in the dialysate can be determined by calculating the total gas phase pressure difference between the dialysate and the base reacted dialysate as described above. A control system can be employed to perform the calculations necessary to determine the concentrations described above. Preferably the volume of base required will be small and similar to the volume of acid required. Likewise, the volume of the pH-buffer measurement system 38 shown in FIG. 3 can have a similar volume to that described for FIG. 2 above.

Determination of the dialysate bicarbonate concentration and pH using the pH-buffer measurement system 38 allows modification of the reconstitution system 43 in order to adjust the pH and bicarbonate concentration to appropriate levels. For example, the reconstitution system 43 can contain a source of bicarbonate of known concentration that can be added to the dialysate flow path 46 at a known flow rate. The flow rate can be adjusted, based on the bicarbonate concentration of the dialysate determined by the pH-buffer measurement system 38, in order to achieve a desired bicarbonate concentration of the dialysate entering the dialyzer 20. Therefore, it is possible to maintain a constant dialysate bicarbonate concentration entering the dialyzer 20. A control system can be employed to perform the calculations necessary to determine the addition rate of bicarbonate from the reconstitution system 43 described above.

Figure 4:
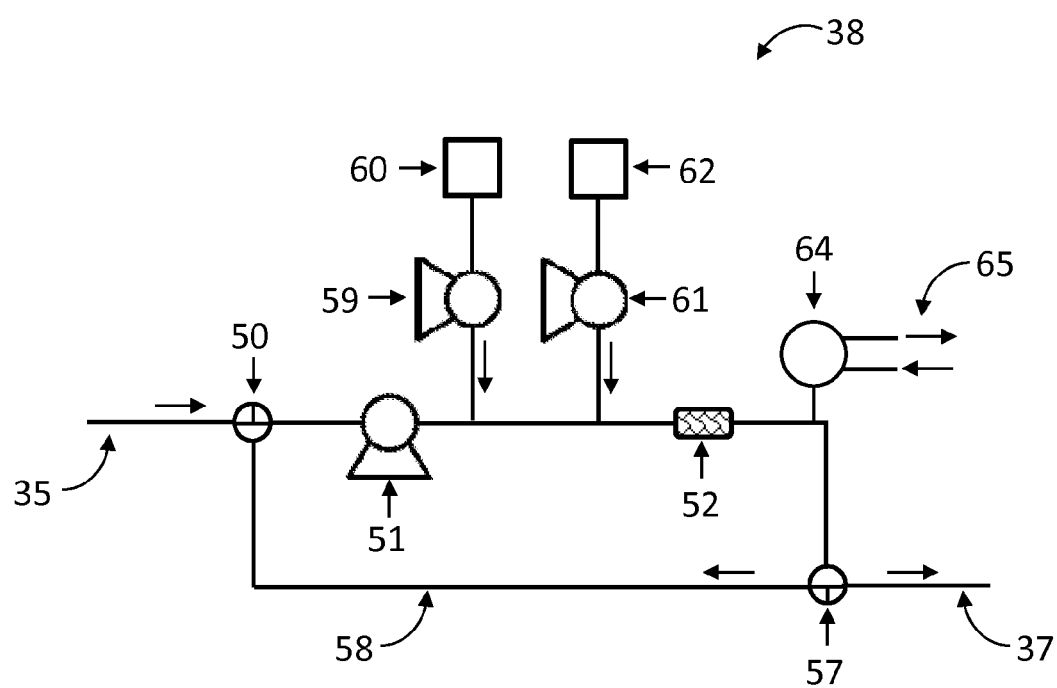
FIG. 4 is a pH-buffer measurement system utilizing a thermal conductivity sensor and an acid and base feed.

FIG. 4 is a flow diagram of a pH-buffer measurement system 38 similar to the one shown in FIG. 3 except instead of a measurement chamber 53 and pressure sensor 56, a thermal conductivity sensor 64 is utilized to determine the carbon dioxide concentration in dialysate. The operation of the pH-buffer measurement system 38 shown in FIG. 4 is the same as that described above for FIGS. 2 and 3. The thermal conductivity sensor 64 works by measuring the thermal conductivity of gases in equilibrium with a liquid solution, such as dialysate. The thermal conductivity of a gas is the ability of the gas to transfer heat. Certain gases have a unique thermal conductivity, including carbon dioxide, which can be measured in order to quantify the amount of a specific gas present. An example of a commercially available thermal conductivity sensor is the Orbisphere In-Line Conductivity Sensor sold by Hach Lange (Dusseldorf, Germany). Other suitable sensors known in the art for the intended use can be used. The Orbisphere sensor operates by allowing a small volume of gas contained in a liquid solution to diffuse across a diffusion membrane, where its thermal conductivity is measured. The Orbisphere sensor can be periodically flushed with a purge gas, after which the gas to be measured diffuses from the liquid solution through the membrane, changing the thermal conductivity of the gas surrounding the thermal conductivity sensor. The rate of change of thermal conductivity is used to calculate the concentration of gas. The purge gas required can include nitrogen and other suitable gases known in the art, and can be added to the thermal conductivity sensor 64 through lines 65 shown in FIG. 4. The purge gas can be contained in a small cartridge or reservoir (not shown) similar in size to the acid or base reservoirs 60 and 62, respectively. Other thermal conductivity sensors with the ability to measure the carbon dioxide concentration in a liquid sample may also be used.

The use of the base feed system 61 and 62 shown in FIG. 4, and described above, is optional. In certain cases the thermal conductivity sensor 64 will be capable of directly measuring the carbon dioxide in the dialysate and acidified dialysate. However, in other embodiments, it may be useful to measure the thermal conductivity response to base reacted dialysate in order to remove measurement noise due to other gases present in the dialysate. A control system can be employed to perform the calculations necessary to determine the concentrations described above.

Figure 5:
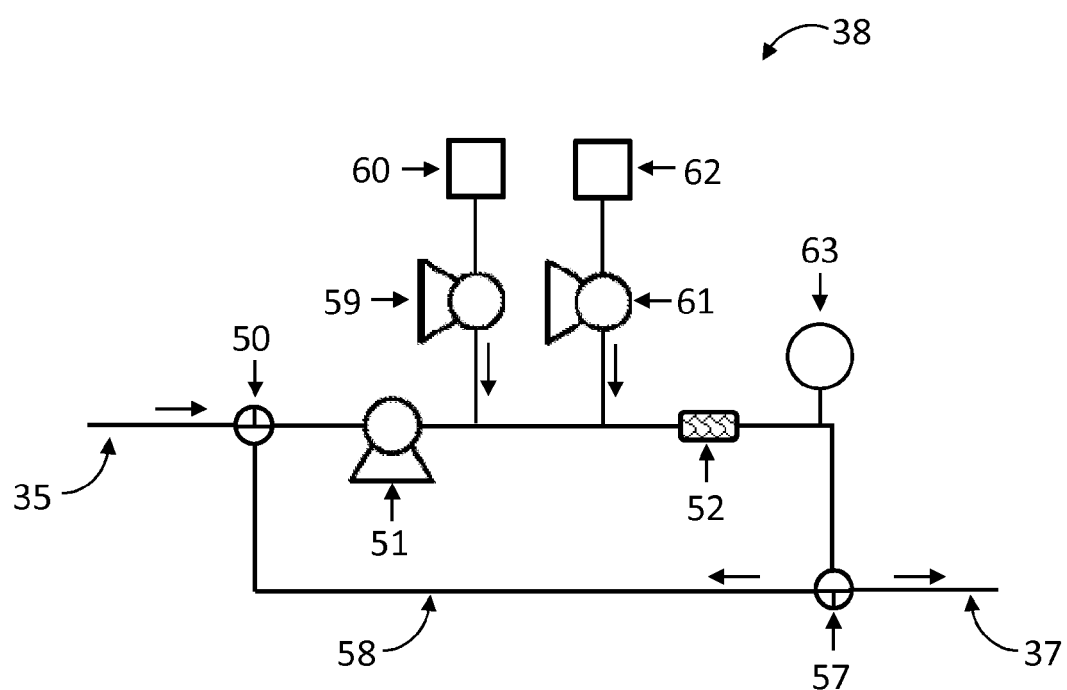
FIG. 5 is a pH-buffer measurement system utilizing an electrical conductivity sensor and an acid and base feed.

FIG. 5 is a flow diagram of a pH-buffer measurement system 38 similar to the one shown in FIG. 4 except an electrical conductivity sensor 63 (also referred to as a conductivity sensor) can be used instead of a thermal conductivity sensor 64. The operation of the pH-buffer measurement system 38 shown in FIG. 5 is the same as that described above for FIGS. 2, 3, and 4. The pH-buffer measurement system 38 of FIG. 5 relies on conductivity differences between the dialysate, acidified dialysate and base reacted dialysate in order to calculate the pH and bicarbonate in the dialysate. The conductivity difference between the dialysate and acidified dialysate can be used to determine the concentration of bicarbonate in the dialysate. All of the solutes in the dialysate will remain constant before and after acidification, except bicarbonate and carbon dioxide. The acidified dialysate will have no bicarbonate present and additional carbon dioxide. Because the contribution of conductivity from bicarbonate is much greater than the contribution from carbon dioxide, the difference in conductivity can be used as a measure of the bicarbonate concentration in the dialysate. Likewise, the base reacted dialysate will convert carbon dioxide in the dialysate to bicarbonate, so the difference in conductivity between base reacted dialysate and the non-reacted dialysate will be related to the concentration of carbon dioxide in the dialysate. The acid and base feeds will contribute additional conductivity to the dialysate, so accurate knowledge of the concentration and volume added will be required, in order to correct for changes in conductivity from the acid and base.

Figure 6:
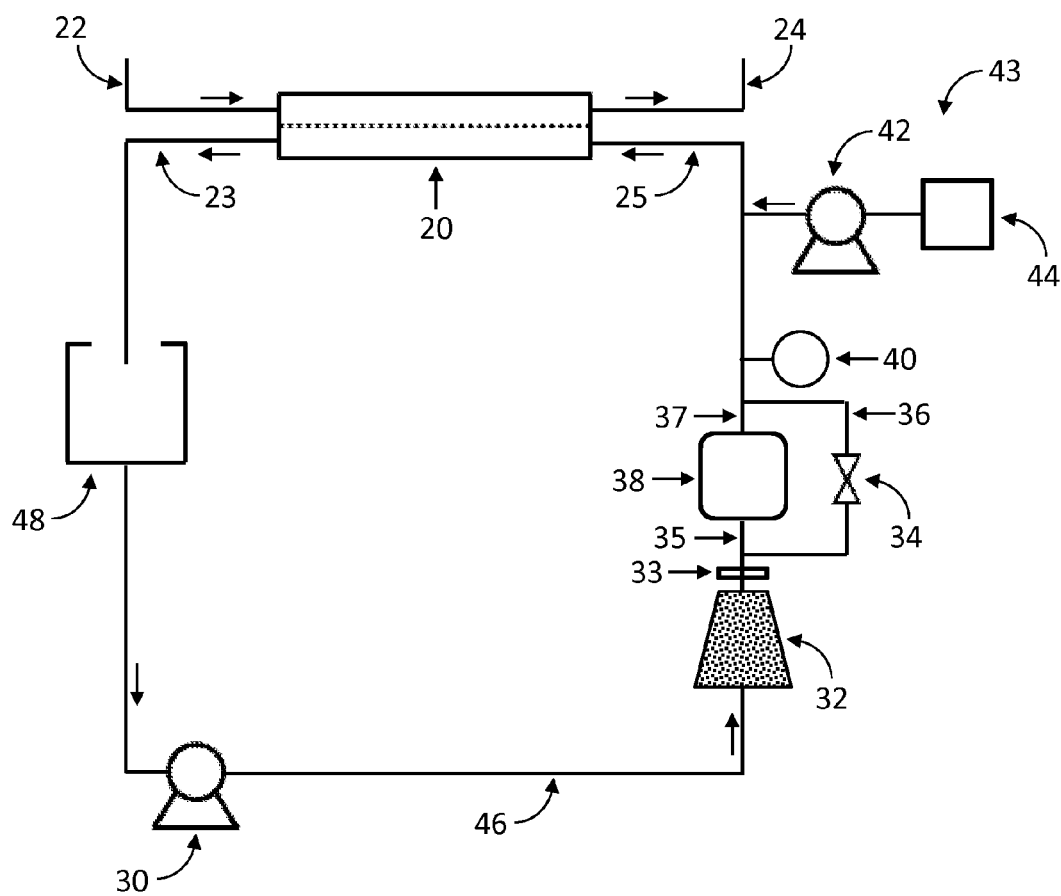
FIG. 6 is a flow diagram of a dialysate regeneration system with an open, non-fixed volume dialysate flow path and a pH-buffer measurement system.

FIG. 6 is an example of a dialysis system similar to that shown in FIG. 1. However, the dialysate flow path 46 shown in FIG. 6 includes an open dialysate reservoir 48. Dialysate reservoir 48 can contain a variable volume. The dialysate fluid contained in dialysate reservoir 48 can vary during the course of a hemodialysis run. Specifically, the volume will increase as ultrafiltrate is removed from the patient by filtration across dialyzer 20. Control of net ultrafiltration may be accomplished by a variety of means known in the art, such as balance chambers and an ultrafiltration (UF) metering pump, duplex metering pumps and a UF metering pump, and trans-membrane pressure regulators with mass or volume measurement (not shown). As used herein, the term ultrafiltrate includes fluid contained in the dialysate reservoir 48.

Hemofiltration, Hemodiafiltration and Peritoneal Dialysis Applications

Figure 7:
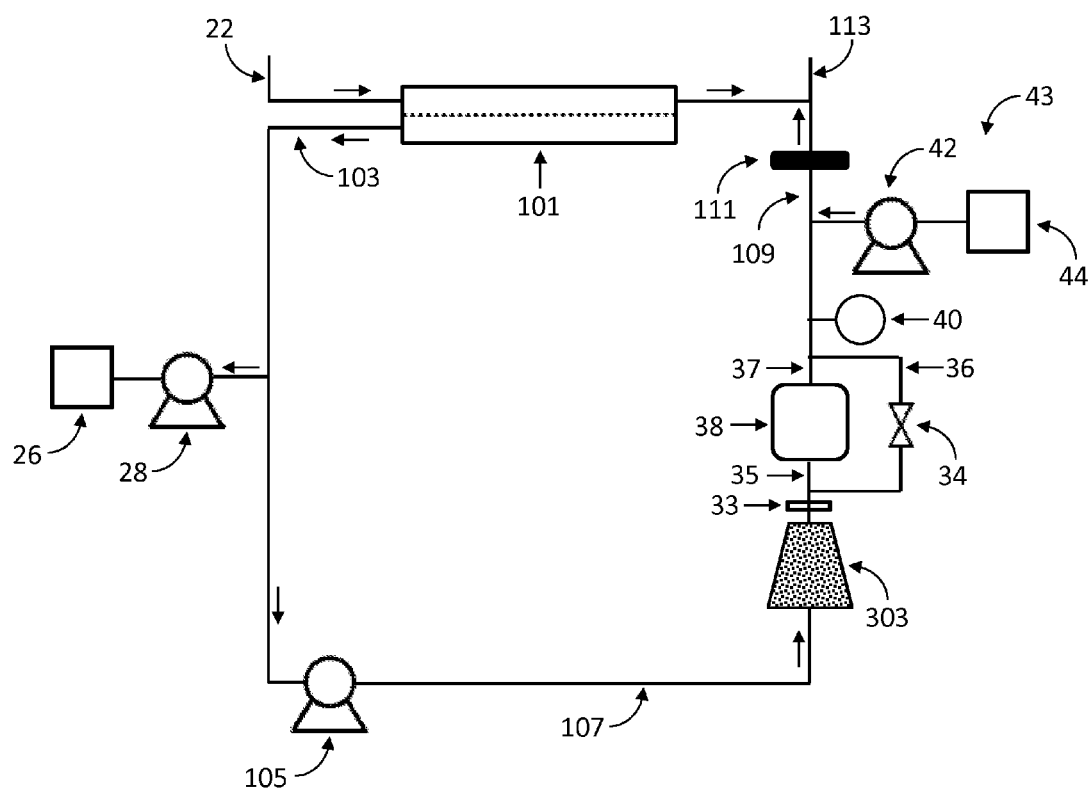
FIG. 7 is a flow diagram of a hemofiltration regeneration system with a controlled compliant filtration flow path and a pH-buffer measurement system.

FIG. 7 shows a flow diagram for a hemofiltration system utilizing a filtrate regeneration unit 303 and a potassium management system 38. The blood enters via line 22 to a hemofilter 101 and a portion is filtered across membranes contained in the hemofilter 101. The hemofilter 101 can include a hollow-fiber dialyzer, plate-and-frame dialyzer, or other suitable hemofilters. The hemofilter 101 can contain high flux or low flux membranes made from polysulfone, polyethersulfone, poly(methyl methacrylate), cellulose, modified-cellulose or other suitable materials. The filtration pump 105 determines the amount of filtrate coming across the hemofilter. The filtrate 103 exiting the hemofilter 101 flows past an ultrafiltration pump 28 whereby ultrafiltrate is removed from the filtrate and collected in an ultrafiltration reservoir 26. The filtrate then passes through a filtrate regeneration unit 303, degasser 33, pH-buffer measurement system 38, and reconstitution system 43 as described above. The regenerated filtrate 109 then passes through a microbial filter 111 before being directly infused into the blood as replacement fluid. The microbial filter 111 could include an ultrafilter filter, sterile filter, or other suitable microbial filters. The microbial filter 111 can contain membranes made from the same materials suitable for the hemofilter, preferably with pore sizes 0.2 microns or smaller. The microbial filter 111 may remove viable and non-viable organisms, microorganisms, and endotoxins. The microbial filter may be a single filter, or multiple filters, including redundant filters. The hemofiltration system shown in FIG. 7 has a controlled compliant filtrate flow path 107. In certain embodiments, the flow path 107 can be non-compliant or non-expandable. Hemofiltration has certain benefits over hemodialysis including higher convective clearance which increases the clearance rate of middle molecular weight species like beta-2-microglobulin.

Figure 8:
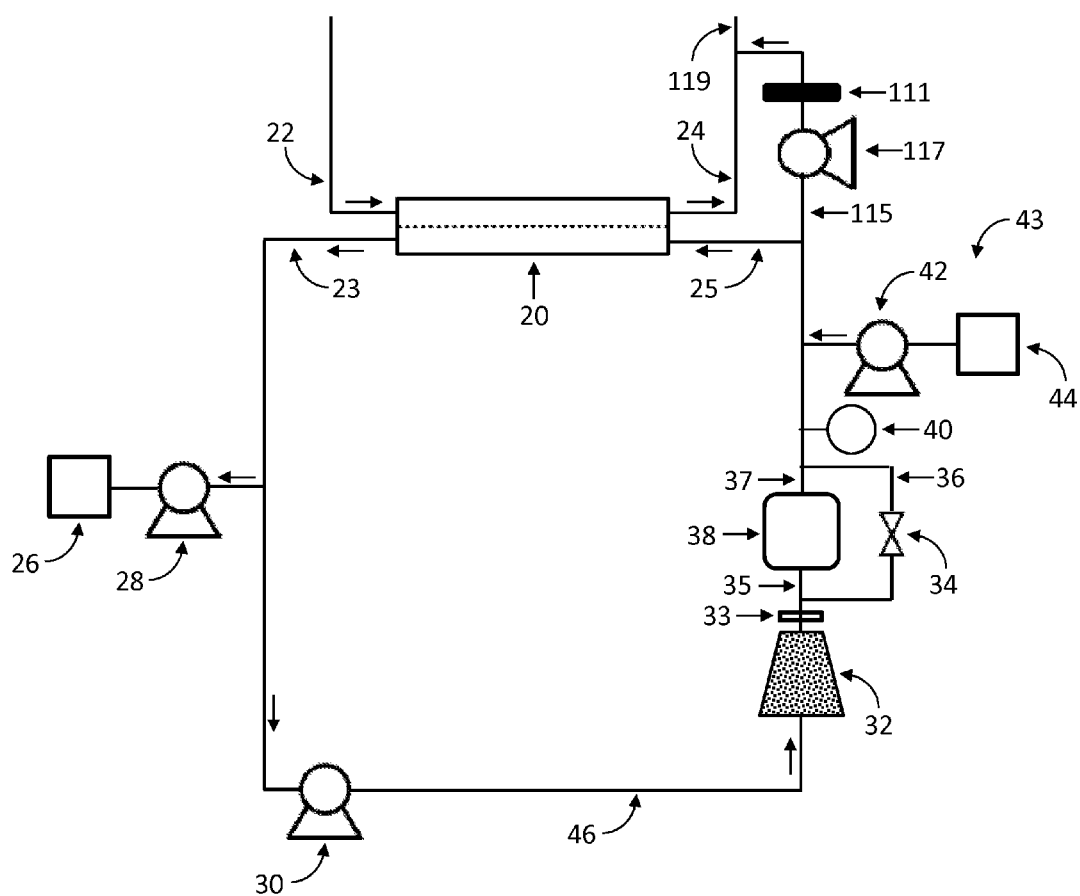
FIG. 8 is a flow diagram of a hemodiafiltration regeneration system with a controlled compliant hemodiafiltration flow path and a pH-buffer measurement system.

FIG. 8 shows a flow diagram for a hemodiafiltration system utilizing a sorbent system 32 and a pH-buffer measurement system 38. The blood enters via line 22 to a dialyzer 20 and a portion is filtered across membranes contained in the dialyzer 20. The dialyzer 20 can include a hollow-fiber dialyzer, plate-and-frame dialyzer, or other types of dialyzers. The dialyzer 20 can contain high flux or low flux membranes made from polysulfone, polyethersulfone, poly(methyl methacrylate), cellulose, modified-cellulose or other suitable materials. The dialysate 23 exiting the dialyzer 20 flows past an ultrafiltration pump 28 whereby a volume of fluid is removed from the dialysate and collected in an ultrafiltration reservoir 26. The dialysate is recirculated in the dialysate flow path 46 with a dialysate pump 30. The dialysate then passes through a sorbent system 32, degasser 33, pH-buffer measurement system 38, and reconstitution system 43 as described above. A portion of the regenerated dialysate 115 is removed from the dialysate flow path 46 with the replacement fluid pump 117 and passed through a microbial filter 111 and then directly infused into the blood as replacement fluid. The microbial filter 111 can include an ultrafilter filter, sterile filter, or other suitable microbial filters. The microbial filter 111 can contain membranes made from the same materials suitable for the dialyzer, preferably with pore sizes 0.2 microns or smaller. The microbial filter 111 may remove both viable organisms and endotoxin. The microbial filter 111 may be a single filter, or multiple filters, including redundant filters. The hemodiafiltration system shown in FIG. 10 has a controlled compliant dialysate flow path 46. In certain embodiments, the flow path 46 can be non-controlled compliant or have a non-expandable volume. Hemodiafiltration combines the benefits achieved with hemodialysis and hemofiltration, including maximum small molecule diffusive clearance and maximum middle molecule convective clearance.

Figure 9:
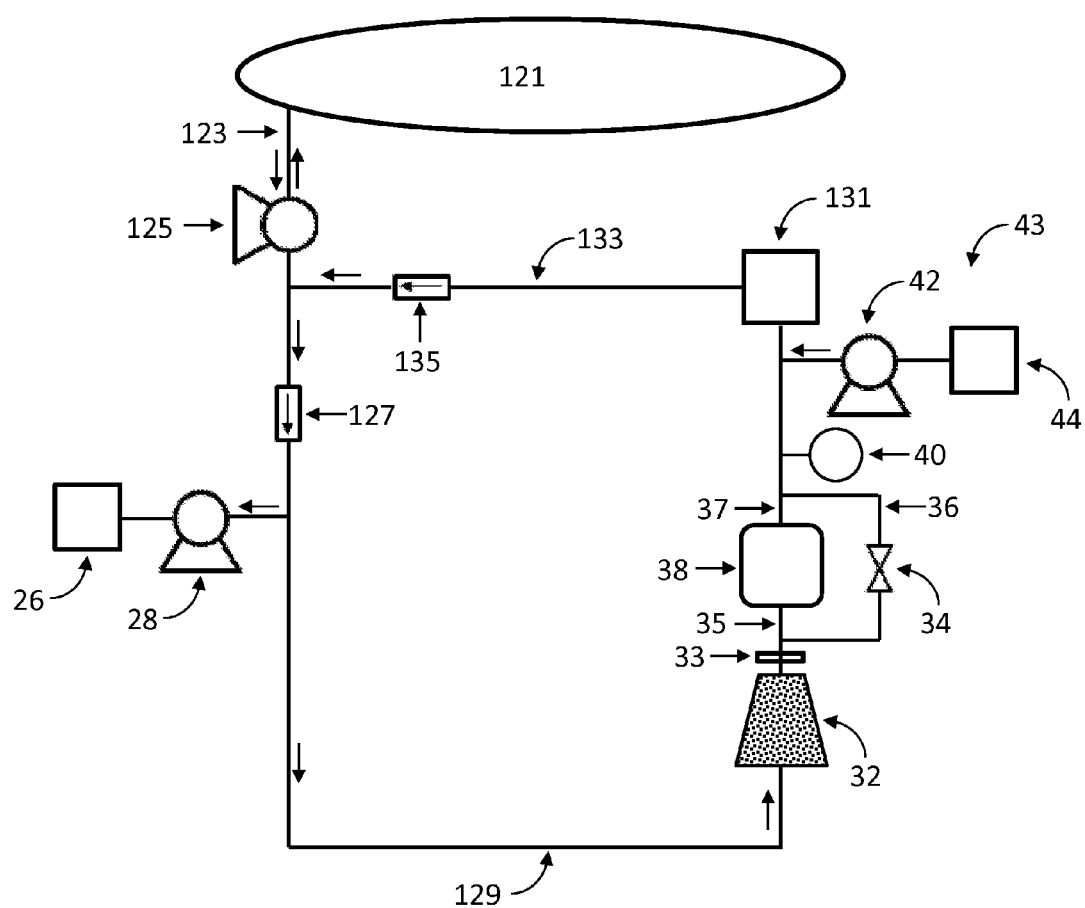
FIG. 9 is a flow diagram of a peritoneal dialysate regeneration system and a pH-buffer measurement system.

FIG. 9 shows a flow diagram for a peritoneal dialysis system utilizing a sorbent system 32 and a pH-buffer measurement system 38. Initially, a patient's peritoneal cavity 121 is filled with a certain volume of dialysate. After a certain period of time, spent dialysate is drawn out of the peritoneal cavity 121 through a catheter 123 with a reversible dialysate pump 125. The spent dialysate flows through a check valve 127 and is prevented from flowing through flow line 133 because of check valve 135. A check valve only allows fluid to flow in one direction within a flow path. The arrows shown on check valves 127 and 133 indicate the direction fluid can flow through them. The spent dialysate continues through the sorbent system 32 via flow path 129 to a degasser 33, pH-buffer measurement system 38 and the reconstitution system 43. In certain embodiments, the flow path 129 can have the controlled compliant feature as defined herein. In other embodiments, the flow path 129 is not controlled compliant. In the case of peritoneal dialysis, the reconstitution system 43 can include infusate containing high levels of glucose or icodextrin in certain embodiments. The regenerated dialysate is collected in a dialysate reservoir 131. After a desired amount of regenerated dialysate has been collected in the dialysate reservoir 131 the dialysate pump 125 can be reversed and fluid can be drawn out of the dialysate reservoir 131. The fluid flows through a check valve 135 and can be directed through the catheter 123 back into the peritoneal cavity. One of ordinary skill in the art will recognize that other configurations of pumps and valves can accomplish the same function, for example, valves 127 and 135 can be combined into a single 3-way valve, or pump 125 may be non-reversible if valves 127 and 135 are 2-way valves and pump 125 is placed downstream from valve 127.

Peritoneal dialysis can be continued until the dialysate regeneration system is exhausted or until the therapy is complete. At the end of a therapy, the patient will have collected a certain volume of ultrafiltrate in their peritoneal cavity. The ultrafiltrate can be removed using the ultrafiltration pump 28 and collected in the ultrafiltration reservoir 26. Likewise, during the therapy, while spent dialysate is being removed from the patient, a portion of the spent dialysate can be removed as ultrafiltrate with the ultrafiltrate pump 28. However, the amount of ultrafiltrate a patient generates is variable and depends on several factors including properties of their peritoneum, dialysate composition, and patient fluid volume, or overload. Therefore, care must be taken when operating the ultrafiltrate pump 28 during the therapy in order to avoid depleting the dialysate contained in the peritoneal cavity 121.

The FIG.'s and specific examples provided herein illustrate a possible embodiment of the invention and are non-limiting with respect to the specific physical geometries of the various components depicted in the illustrations. It will be apparent to one skilled in the art that various combinations and/or modifications can be made in the systems and methods described herein depending upon the specific needs for operation. Moreover, features illustrated or described as being part of one embodiment may be used on another embodiment to yield a still further embodiment.

What is claimed is:

1. A pH-buffer measurement system for a dialysis system, comprising:
   at least one source for modifying the pH of a fluid entering the pH-buffer measurement system, wherein at least one source for modifying the pH is selected from an acid source and a base source, and wherein the acid source adds an acid equivalent to provide an acid reacted fluid and the base source adds a base equivalent to provide a base reacted fluid, and wherein the at least one source is in fluid communication with a dialysate flow path; and
   a component, positioned downstream of the at least one source for modifying the pH of the fluid entering the pH-buffer measurement system, for determining a fluid characteristic of the acid reacted fluid or the base reacted fluid; wherein the fluid characteristic that is measured is any one of a gas phase pressure, an electrical conductivity, or thermal conductivity,
   a sorbent system in the dialysate flow path;
   wherein the acid reacted fluid comprises at least a portion of the acid equivalent reacted with buffer in the fluid entering the pH-buffer measurement system, and the base reacted fluid comprises at least a portion of the base equivalent reacted with buffer in the fluid entering the pH-buffer measurement system.

2. The system of claim 1, wherein the component determines a fluid characteristic of an unreacted fluid.

3. The system of claim 1, further comprising a static mixer downstream from the at least one source for modifying the pH of the fluid entering the pH-buffer measurement system.

4. The system of claim 1, further comprising one or more pumps for pumping fluid into and out of the pH-buffer measurement system.

5. The system of claim 1, wherein the pH-buffer measurement system is configured to determine pH, buffer content, or both of the fluid by taking a difference between a first value of the fluid characteristic of the fluid entering the pH-buffer measurement system and a second value of the fluid characteristic of the acid reacted fluid or the base reacted fluid.

6. The system of claim 1, wherein the pH-buffer measurement system determines a pH, buffer content or both of the fluid by taking a difference between a first value of the fluid characteristic of the fluid entering the pH-buffer measurement system and a second value of the fluid characteristic of an unreacted fluid.

7. The system of claim 1, wherein the component measures a gas phase pressure in an area over the fluid entering the pH-buffer measurement system.

8. The system of claim 1, wherein the component measures a gas phase pressure in an area over the acid reacted fluid or the base reacted fluid.

9. The system of claim 1, wherein the component measures a gas phase thermal conductivity of the fluid entering the pH-buffer measurement system.

10. The system of claim 1, wherein the component measures a gas phase thermal conductivity of the acid reacted fluid or the base reacted fluid.

11. The system of claim 9 or 10, wherein the component measuring the thermal conductivity is configured to be flushed with a purge gas wherein the gas to be measured diffuses from the fluid entering the pH-buffer measurement system, the acid reacted fluid, or the base reacted fluid through a membrane changing the thermal conductivity of a gas surrounding an electrode.

12. The system of claim 11, wherein a rate of change of the thermal conductivity is used to calculate a concentration of a gas.

13. The system of claim 1, wherein the component is configured to measure an electrical conductivity of the acid reacted fluid or the base reacted fluid.

14. The system of claim 1, wherein the component is configured to measure an electrical conductivity of the fluid entering the pH-buffer measurement system.

15. The system of claim 1, wherein the fluid entering the pH-buffer measurement system is dialysate.

16. The system of claim 1, wherein the fluid characteristic comprises a buffer content to be measured, and wherein the buffer content to be measured is bicarbonate content of the fluid.

17. The system of claim 1, wherein the acid source adds acid in a predetermined amount to ensure complete conversion of bicarbonate in the fluid entering the pH-buffer measurement system.

18. The system of claim 1, wherein the acid source adds at least one of acetic acid, citric acid, hydrochloric acid, and phosphoric acid.

19. The system of claim 1, wherein the component has a first measurement chamber to measure a gas phase pressure of the acid reacted fluid or the base reacted fluid, and a second measurement chamber to measure a gas phase pressure of the fluid entering the pH-buffer measurement system.

20. The system of claim 19, further comprising a differential pressure sensor in fluid communication with the first and second measurement chambers.

21. The system of claim 19, wherein the first or second measurement chamber has an air-gap above a gas permeable membrane in fluid communication with a pressure transducer and a vent valve to allow gas to escape from the first or second measurement chamber wherein the pressure transducer measures a pressure of the gas phase above any one of the acid reacted fluid, the base reacted fluid, or the fluid entering the pH-buffer measurement system.

22. The system of claim 1, further comprising a control system to perform calculations necessary for determining the fluid characteristic based on any one of the acid reacted fluid, the base reacted fluid, or the fluid entering the pH-buffer measurement system.

23. A fluid therapy system, comprising:
a dialyzer and a sorbent system in fluid communication with a pH-buffer measurement system to form a dialysate flow path; wherein the pH-buffer measurement system comprises:
at least one source for modifying the pH of a fluid entering the pH-buffer measurement system, the at least one source selected from an acid source and a base source wherein the acid source adds an acid equivalent to provide an acid reacted fluid and the base source adds a base equivalent to provide a base reacted fluid wherein the at least one source is in fluid communication with the dialysate flow path; and
a component positioned downstream of the source for modifying the pH of the fluid entering the pH-buffer measurement system, for determining a fluid characteristic of the acid reacted fluid or the base reacted fluid; wherein the fluid characteristic that is measured is any one of a gas phase pressure, an electrical conductivity, or thermal conductivity; and
a reconstitution system positioned downstream of the pH-buffer measurement system for providing a controlled amount of a buffer to be added to a dialysate to form a second dialysate with a predetermined concentration of the buffer prior to use in the dialyzer,
wherein the pH-buffer measurement system determines the pH, buffer concentration or both of any one of the acid reacted fluid, the base reacted fluid, or the fluid entering the pH-buffer measurement system.

24. The system of claim 23, wherein the buffer is bicarbonate.

25. The system of claim 23, wherein the pH-buffer measurement system is positioned downstream from the sorbent system and a degasser.

26. The system of claim 23, wherein the reconstitution system adjusts the pH and bicarbonate concentration to desired levels.

27. The system of claim 23, further comprising a conductivity sensor connected anywhere along the dialysate flow path.

28. The system of claim 23, wherein fluid in the dialysate flow path is selectively metered into and out of the dialysate flow path.

29. The system of claim 23, wherein the fluid therapy system is a controlled compliant system.

30. The system of claim 29, wherein fluid in the dialysate flow path is selectively metered into and out of the dialysate flow path.

31. The system of claim 23, wherein the fluid therapy system is used for any one of hemodialysis and hemofiltration.

32. A method for determining a pH or buffer content of a fluid in a dialysate flow path, comprising the step of:
modifying the pH of the fluid by adding an acid equivalent from an acid source to provide an acid reacted fluid or adding a base equivalent from a base source to provide a base reacted fluid; and
determining at least one fluid characteristic of the acid reacted fluid or the base reacted fluid by taking a difference between a first value of the fluid characteristic and a second value of the fluid characteristic of the acid reacted fluid or the base reacted fluid;
wherein at least one of the first value of the fluid characteristic and second value of the fluid characteristic is measured downstream of the acid source or the base source in the dialysate flow path, and
wherein the acid reacted fluid comprises at least a portion of the acid equivalent reacted with buffer in the fluid entering the pH-buffer measurement system, and the base reacted fluid comprises at least a portion of the base equivalent reacted with buffer in the fluid entering the pH-buffer measurement system.

33. The method of claim 32, further comprising the step of:
recirculating the acid reacted fluid or the base reacted fluid to allow complete reaction between bicarbonate and an acid to form carbon dioxide to form a recirculated fluid;
measuring the pressure of the recirculated fluid reading to determine an amount of carbon dioxide contained in the recirculated fluid.

34. The method of claim 32, further comprising the step of:
recirculating the fluid to determine total pressure of gases in equilibrium with the fluid, wherein the fluid is a dialysate;
acidifying the dialysate to convert all bicarbonate in the dialysate to carbon dioxide;
measuring a total pressure of gases in equilibrium with the dialysate with a pressure sensor; and
determining a partial pressure of carbon dioxide in the dialysate.

35. The method of claim 32, further comprising the step of flowing the fluid through a static mixer to enhance the mixing between the acid equivalent and the fluid, wherein the fluid is a dialysate.

36. The method of claim 34, further comprising the step of flowing the fluid through any one of a fluid path for hemodialysis, hemofiltration, hemodiafiltration and peritoneal dialysis.

37. A fluid therapy system comprising:
a fluid flow path in fluid communication with a dialyzer, a sorbent regeneration unit,
a fluid characteristic management unit, the fluid characteristic management unit being positioned between the sorbent regeneration unit and the dialyzer along a fluid flow, and
a reconstitution system positioned downstream of the fluid characteristic management unit.

38. The fluid therapy system of claim 37, wherein the fluid characteristic management unit is a pH-buffer management unit.

39. The fluid therapy system of claim 37, wherein the fluid characteristic management unit is a potassium management unit.

40. The fluid therapy system of claim 37, further comprising a degasser in fluid communication with the fluid flow path and being positioned downstream of the sorbent regeneration unit along the fluid flow.

41. The fluid therapy system of claim 37, further comprising a bypass flow path diverting a portion of the fluid flow from the fluid characteristic management unit.

42. The fluid therapy system of claim 37, further comprising a conductivity sensor in fluid communication with the fluid flow path and being positioned downstream of the fluid characteristic management unit along the fluid flow.

43. The fluid therapy system of claim 37, wherein the fluid characteristic management unit includes at least one of an inlet for an acid feed and an inlet for a base feed.

44. The fluid therapy system of claim 37, wherein the fluid characteristic management unit includes at least one of a thermal conductivity sensor and an electrical conductivity sensor.

45. The fluid therapy system of claim 37, further comprising a replacement flow loop in fluid communication with the fluid flow path and positioned downstream of the fluid characteristic management unit, the replacement flow loop transporting a portion of a regenerated fluid out of the sorbent regeneration unit directly into the blood of a subject and bypassing the dialyzer.

46. The fluid therapy system of claim 37, further comprising an open dialysate reservoir in fluid communication with the fluid flow path and being positioned upstream of the sorbent regeneration unit along the fluid flow.

* * * * *